United States Patent [19]
Yu et al.

[11] Patent Number: 5,643,963
[45] Date of Patent: *Jul. 1, 1997

[54] METHOD OF USING ISOCITRIC ACID FOR TREATING WRINKLES

[75] Inventors: Ruey J. Yu, Ambler; Eugene J. Van Scott, Abington, both of Pa.

[73] Assignee: Tristrata Technology, Inc., Wilmington, Del.

[*] Notice: The term of this patent shall not extend beyond the expiration date of Pat. No. 5,091,171.

[21] Appl. No.: 471,523

[22] Filed: Jun. 6, 1995

Related U.S. Application Data

[63] Continuation of Ser. No. 135,841, Oct. 7, 1993, which is a continuation of Ser. No. 840,149, Feb. 24, 1992, abandoned, which is a division of Ser. No. 393,749, Aug. 15, 1989, Pat. No. 5,091,171, which is a continuation-in-part of Ser. No. 945,680, Dec. 23, 1986, abandoned.

[51] Int. Cl.⁶ ............................. A61K 31/19; A61K 7/48
[52] U.S. Cl. .......................... 514/574; 514/844; 514/847; 514/873; 514/941
[58] Field of Search ............................... 514/557, 574, 514/844, 847, 873, 941

[56] References Cited

U.S. PATENT DOCUMENTS

| | | | |
|---|---|---|---|
| 1,772,975 | 8/1930 | Wieland | 514/557 |
| 2,118,566 | 5/1938 | De Wayne | 167/90 |
| 3,227,616 | 1/1966 | Van Wessem et al. | 167/91 |
| 3,666,863 | 5/1972 | Swanback | 424/316 |
| 3,689,668 | 9/1972 | Piette | 514/532 |
| 3,806,593 | 4/1974 | Swanback et al. | 424/28 |
| 3,879,537 | 4/1975 | Van Scott et al. | 424/311 |
| 3,920,835 | 11/1975 | Van Scott et al. | 514/557 |
| 3,984,566 | 10/1976 | Van Scott et al. | 424/283 |
| 3,988,470 | 10/1976 | Van Scott et al. | 424/283 |
| 3,991,184 | 11/1976 | Kludas et al. | 424/177 |
| 4,021,572 | 5/1977 | Van Scott et al. | 424/317 |
| 4,053,630 | 10/1977 | Yu et al. | 514/494 |
| 4,105,782 | 8/1978 | Yu et al. | 424/283 |
| 4,105,783 | 8/1978 | Yu et al. | 424/283 |
| 4,197,316 | 4/1980 | Yu et al. | 424/317 |
| 4,234,599 | 11/1980 | Van Scott et al. | 424/279 |
| 4,246,261 | 1/1981 | Van Scott et al. | 424/240 |
| 4,287,214 | 9/1981 | Van Scott et al. | 424/346 |
| 4,363,815 | 12/1982 | Yu et al. | 424/274 |
| 4,380,549 | 4/1983 | Van Scott et al. | 424/317 |
| 4,518,789 | 5/1985 | Yu et al. | 560/105 |
| 4,612,185 | 9/1986 | Barrett et al. | 514/558 |
| 4,929,722 | 5/1990 | Partain et al. | 536/20 |
| 4,983,382 | 1/1991 | Wilmott et al. | 424/62 |
| 5,021,451 | 6/1991 | McLane et al. | 514/460 |
| 5,091,171 | 2/1992 | Yu et al. | 424/642 |
| 5,093,109 | 3/1992 | Mausner | 424/63 |
| 5,108,751 | 4/1992 | Hagan et al. | 424/401 |
| 5,153,230 | 10/1992 | Jeffery | 514/847 |
| 5,389,677 | 2/1995 | Yu et al. | 514/557 |
| 5,470,880 | 11/1995 | Yu et al. | 514/574 |

FOREIGN PATENT DOCUMENTS

| | | |
|---|---|---|
| 64399 | 7/1975 | Australia . |
| 007785 | 2/1980 | European Pat. Off. . |
| 086070 | 8/1983 | European Pat. Off. . |
| 413528 | 2/1991 | European Pat. Off. . |
| 1439834 | 4/1966 | France . |
| 2517413 | 11/1975 | Germany . |
| 3540175 | 5/1987 | Germany . |
| 58-8007 | 1/1983 | Japan . |
| 752066 | 4/1975 | South Africa . |

OTHER PUBLICATIONS

Bergwein, K. *Kosmetik*, 16:555–557, (1967).
Gattefosse, R.M. *Formulary of Perfumes and Cosmetics*, Chemical Publishing Co., Inc., (1959) pp. 214–215.
Hodgman, et al. *Handbook of Chemistry and Physics*, The Chemical Rubbre Publishing Co., pp. 1752–1757 (1984).
Webster's Ninth New Collegiate Dictionary, Merriam–Webster Inc. (1985) p. 1272.
Derwent Abstract 86–064922[10] for JP 61–015810 (Jan. 23, 1986), Nonogawa, Shuji YG.
Derwent Abstract 85–228562[37] for SU 1140785 (Feb. 23, 1985), Gerchikov, et al.
Chemical Abstracts 70:14330q (1967), Durafrourd.
Chemical Abstracts 85:25286r (1976), Hadhary, et al.
Chemical Abstracts 108:210190m (1988).
Dorland's Medical Dictionary, 26th Ed., Saunders, Philadelphia, PA (1981) 647, 696–97.
Neostrata Company Notice (1992).
Merck Index, 10th Ed., Rathway, New Jersey, (1983) p. 768.
Weiss, J.S., M.D., et al., "Topical Tretinoin in the Treatment of Aging Skin".
J. Amer. Acad. of Dermatology, vol. 19 (1988) pp. 169–175.
Weiss, J.S., M.D., et al., "Topical Tretinoin Improves Photoaged Skin: A Double–blind Vehicle Controlled Study", *J. Amer. Medical Assn.*, vol. 259, No. 4 (1988) pp. 527–532.
Moisturizing & Emolliency Documentary, Unusual Moisturizers and Emollients: Patent Digest for 1966–1977, Cosmetics and Toiletries, vol. 93, Apr. 1978, pp. 55–60.
Chemical Abstracts 65864w, Bleehen, S.S., Skin Bleaching Preparations, vol. 88 (1978).
Chemical Abstracts 79710x, Juhlin, L.A., Dermatologically Useful Composition, vol. 84 (1976).
Fredriksson, T. et al., Urea Creams in the Treatment of Dry Skin and Hand Dermatitis, Pharmacology and Therapeutics, pp. 442–444 (1975).
Blair, C., The Action of a Urea–Lactic Acid Ointment in Ichthyosis, *British Journal of Dermatology* vol. 94 pp.145–153 (1976).
Van Scott et al., Control of Keratinization with α–Hydroxyacids and Related Compounds, *Arch Dermatol* vol. 110 pp. 586–90 (1974).

(List continued on next page.)

*Primary Examiner*—James J. Seidleck
*Assistant Examiner*—Michael A. Williamson
*Attorney, Agent, or Firm*—Foley & Lardner

[57] ABSTRACT

Methods for visibly reducing a skin wrinkle and for reversing the effect of aging on human facial skin involving comprising topically applying to the wrinkle and/or affected facial skin isocitric acid.

20 Claims, No Drawings

OTHER PUBLICATIONS

Grice, K., et al., Urea and Retinoic Acid in Ichthyosis and Their Effect on Transepidermal Water Loss and Water Holding Capacity of Stratum Corneum, *Acta Dermatovener* vol. 53 pp. 114–118 (1973).

Harry, R.G., The Principles and Practice of Modern Cosmetics, 6th Ed., Chapters 6 and 39, (1973).

Goldberg, R.L., et al. Correlation of Skin Feel of Emollients to Their Chemical Structure, *J. Soc. Cosmet. Chem.*, vol. 22 pp. 635–654 (1971).

Sedik, F., O–T–C Products for Corns, Calluses, Warts, *Journal of the American Pharmaceutical Association*, vol. NS10, No. 1, pp. 8–12 (1970).

Osipow, L.I., A Buffering Humectant for Cosmetics, *Drug and Cosmetic Industry*, vol. 88, No. 4, pp. 438–515 (1961).

Stern, E.C., Topical Application of Lactic Acid in the Treatment and Prevention of Certain Disorders of the Skin, *The Urologic and Cutaneous Review*, vol. 50, No. 2, pp. 106–107 (1946).

Darr, D., Topical Vitamin C Protects Skin from Ultraviolet Radiation–Induced Damage, *British Journal of Dermatology*, vol. 127, pp.247–53 (1992).

Aggarwal, R.R., et al., A Clinical Trial with Cotaryl Cream in Hyperkeratotic Skin Conditions, *Indian J. Dermatol. Venerbol.*, vol. 45, No. 6, pp. 442–444.

METHOD OF USING ISOCITRIC ACID FOR TREATING WRINKLES

This application is a continuation of application Ser. No. 08/135,841, filed Oct. 7, 1993, which is a continuation of U.S. application Ser. No. 07/840,149, filed Feb. 24, 1992, now abandoned, which is a divisional of U.S. application Ser. No. 07/393,749, filed on Aug. 15, 1989, now U.S. Pat. No. 5,091,171, which is a continuation-in-part of U.S. application Ser. No. 06/945,680, filed on Dec. 23, 1986, now abandoned.

FIELD OF THE INVENTION

This invention relates generally to therapeutic treatment as well as preventive measures for cosmetic conditions and dermatologic disorders by topical administration of amphoteric compositions or polymeric forms of alpha hydroxyacids, alpha ketoacids and related compounds. We initially discovered that alpha hydroxy or keto acids and their derivatives were effective in the topical treatment of disease conditions such as dry skin, ichthyosis, eczema, palmar and plantar hyperkeratoses, dandruff, acne and warts.

We have now discovered that amphoteric compositions and polymeric forms of alpha hydroxyacids, alpha ketoacids and related compounds on topical administration are therapeutically effective for various cosmetic conditions and dermatologic disorders.

BRIEF DESCRIPTION OF THE PRIOR ART

In our prior U.S. Pat. No. 3,879,537 entitled "Treatment of Ichthyosiform Dermatoses" we described and claimed the use of certain alpha hydroxyacids, alpha ketoacids and related compounds for topical treatment of fish-scale like ichthyotic conditions in humans. In our U.S. Pat. No. 3,920,835 entitled "Treatment of Disturbed Keratinization" we described and claimed the use of these alpha hydroxyacids, alpha ketoacids and their derivatives for topical treatment of dandruff, acne, and palmar and plantar hyperkeratosis.

In our prior U.S. Pat. No. 4,105,783 entitled "Treatment of Dry Skin" we described and claimed the use of alpha hydroxyacids, alpha ketoacids and their derivatives for topical treatment of dry skin. In our recent U.S. Pat. No. 4,246,261 entitled "Additives Enhancing Topical Corticosteroid Action" we described and claimed that alpha hydroxyacids, alpha ketoacids and their derivatives, could greatly enhance the therapeutic efficacy of corticosteroids in topical treatment of psoriasis, eczema, seborrheic dermatitis and other inflammatory skin conditions.

In our more recent U.S. Pat. No. 4,363,815 entitled "Alpha Hydroxyacids, Alpha Ketoacids and Their Use in Treating Skin Conditions" we described and claimed that alpha hydroxyacids and alpha ketoacids related to or originating from amino acids, whether or not found in proteins, were effective in topical treatment of skin disorders associated with disturbed keratinization or inflammation. These skin disorders include dry skin, ichthyosis, palmar and plantar hyperkeratosis, dandruff, Darier's disease, lichen simplex chronicus, keratoses, acne, psoriasis, eczema, pruritus, warts and herpes.

In our most recent patent application Ser. No. 945,680 filed Dec. 23, 1986 and entitled "Additives Enhancing Topical Actions of Therapeutic Agents" we described and claimed that incorporation of an alpha hydroxyacid or related compound can substantially enhance therapeutic actions of cosmetic and pharmaceutical agents.

SUMMARY OF THE INVENTION

There is no doubt that alpha hydroxyacids, alpha ketoacids and related compounds are therapeutically effective for topical treatment of various cosmetic conditions and dermatologic disorders including dry skin, acne, dandruff, keratoses, age spots, wrinkles and disturbed keratinization. However, the compositions containing these acids may irritate human skin on repeated topical applications due to lower pH of the formulations. The irritation may range from a sensation of tingling, itching and burning to clinical signs of redness and peeling. Causes for such irritation may arise from the following:

Upper layers of normal skin have a pH of 4.2 to 5.6, but the compositions containing most alpha hydroxyacids or alpha ketoacids have pH values of less than 3.0. For example, a topical formulation containing 7.6% (1M) glycolic acid has a pH of 1.9, and a composition containing 9% (1M) lactic acid has the same pH of 1.9. These compositions of lower pH on repeated topical applications can cause a drastic pH decrease in the stratum corneum of human skin, and provoke disturbances in intercorneocyte bondings resulting in adverse skin reactions, especially to some individuals with sensitive skin.

Moreover, with today's state of the art it is still very difficult to formulate a lotion, cream or ointment emulsion which contains a free acid form of the alpha hydroxyacid, and which is physically stable as a commercial product for cosmetic or pharmaceutical use.

When a formulation containing an alpha hydroxyacid or alpha ketoacid is reacted equimolarly or equinormally with a metallic alkali such as sodium hydroxide or potassium hydroxide the composition becomes therapeutically ineffective. The reasons for such loss of therapeutic effects are believed to be as follows:

The intact skin of humans is a very effective barrier to many natural and synthetic substances. Cosmetic and pharmaceutical agents may be pharmacologically effective by oral or other systematic administration, but many of them are much less or totally ineffective on topical application to the skin. Topical effectiveness of a pharmaceutical agent depends on two major factors; (a) bioavailability of the active ingredient in the topical preparation and (b) percutaneous absorption, penetration and distribution of the active ingredient to the target site in the skin. For example, a topical preparation containing 5% salicylic acid is therapeutically effective as a keratolytic, but that containing 5% sodium salicylate is not an effective product. The reason for such difference is that salicylic acid is in bioavailable form and can penetrate the stratum corneum, but sodium salicylate is not in bioavailable form and cannot penetrate the stratum corneum of the skin.

In the case of alpha hydroxyacids, a topical preparation containing 5% glycolic acid is therapeutically effective for dry skin, but that containing 5% sodium glycollate is not effective. The same is true in case of 5% lactic acid versus 5% sodium lactate. The reason for such difference is that both glycolic acid and lactic acid are in bioavailable forms and can readily penetrate the stratum corneum, but sodium glycollate and sodium lactate are not in bioavailable forms and cannot penetrate the stratum corneum of the skin.

When a formulation containing an alpha hydroxyacid or alpha ketoacid is reacted equimolarly or equinormally with ammonium hydroxide or an organic base of smaller molecule the composition still shows some therapeutic effects for certain cosmetic conditions such as dry skin, but the composition has lost most of its potency for other dermatologic disorders such as wrinkles, keratoses, age spots and skin changes associated with aging.

It has now been discovered that amphoteric compositions containing alpha hydroxyacids, alpha ketoacids or related compounds, and also the compositions containing dimeric or polymeric forms of hydroxyacids overcome the aforementioned shortcomings and retain the therapeutic efficacies for cosmetic conditions and dermatologic disorders. The amphoteric composition contains in combination an amphoteric or pseudoamphoteric compound and at least one of the alpha hydroxyacids, alpha ketoacids or related compounds. Such amphoteric system has a suitable pH, and can release the active form of an alpha hydroxyacid or alpha ketoacid into the skin. The dimeric and polymeric forms of alpha, beta or other hydroxyacids in non-aqueous compositions have a more desired pH than that of the monomeric form of the hydroxyacids. The non-aqueous compositions can be formulated and induced to release the active form of hydroxyacids after the compositions have been topically applied to the skin. The cosmetic conditions and dermatologic disorders in humans and animals, in which the amphoteric compositions containing the dimeric or polymeric forms of hydroxyacids may be useful, include dry skin, dandruff, acne, keratoses, psoriasis, eczema, pruritus, age spots, lentigines, melasmas, wrinkles, warts, blemished skin, hyperpigmented skin, hyperkeratotic skin, inflammatory dermatoses, skin changes associated with aging and as skin cleansers.

DETAILED DESCRIPTION OF THE INVENTION

I. Amphoteric and Pseudoamphoteric Compositions

Amphoteric substances by definition should behave either as an acid or a base, and can be an organic or an inorganic compound. The molecule of an organic amphoteric compound should consist of at least one basic and one acidic group. The basic groups include, for example, amino, imino and guanido groups. The acidic groups include, for example, carboxylic, phosphoric and sulfonic groups. Some examples of organic amphoteric compounds are amino acids, peptides, polypeptides, proteins, creatine, aminoaldonic acids, aminouronic acids, lauryl aminopropylglycine, aminoaldaric acids, neuraminic acid, desulfated heparin, deacetylated hyaluronic acid, hyalobiuronic acid, chondrosine and deacetylated chondroitin.

Inorganic amphoteric compounds are certain metallic oxides such as aluminum oxide and zinc oxide.

Pseudoamphoteric compounds are either structurally related to true amphoteric compounds or capable of inducing the same function when they are incorporated into the compositions containing alpha hydroxyacids or ketoacids. Some examples of pseudoamphoteric compounds are creatinine, stearamidoethyl diethylamine, stearamidoethyl diethanolamine, stearamidopropyl dimethylamine, quaternary ammonium hydroxide and quaternium hydroxide.

The amphoteric composition of the instant invention contains in combination an alpha hydroxyacid or alpha ketoacid and an amphoteric or pseudoamphoteric compound. There are two advantages of utilizing an amphoteric or the like compound in the therapeutic composition containing an alpha hydroxy or ketoacid. These are (a) the overall pH of the composition is raised, so that the composition becomes less or non-irritating to the skin and (b) some alpha hydroxy or ketoacid molecules react with the amphoteric compound to form a quadruple ionic complex which acts as buffering system to control the release of alpha hydroxy or ketoacid into the skin, therefore, eliminating the skin irritation and still retaining the therapeutic efficacies.

The following are some examples. 2-Hydroxyethanoic acid (glycolic acid) 1M aqueous solution has pH 1.9. The pHs of compositions change to 3.0 and 3.2 when arginine 0.5M and creatinine 0.5M respectively are incorporated into the formulations. 2-Hydroxypropanoic acid (lactic acid) 1M aqueous solution has pH 1.9. The pHs of compositions change to 3.1 and 6.9 when arginine 0.5M and 1.0M respectively are incorporated into the formulations. 2-Methyl 2-hydroxypropanoic acid (methyllactic acid) 1M aqueous solution has pH 1.9. The pHs of compositions change to 3.3, 3.4 and 3.2 when 0.5M each of arginine, creatinine and 4-aminobutanoic acid respectively are incorporated into the formulations. 2-Hydroxybutane-1,4-dioic acid (malic acid) 1M aqueous solution has pH 1.8, but the pH of the composition changes to 3.0 when creatinine 0.5M is incorporated into the formulation.

Ideally, an amphoteric compound should contain both anionic and cationic groups or functional groups capable of behaving both as an acid and a base. Although inorganic amphoteric compounds such as aluminum oxide, aluminum hydroxide and zinc oxide may be utilized, organic amphoteric compounds have been found to be more efficient in formulating therapeutic compositions of the instant invention.

Organic amphoteric and pseudoamphoteric compounds may be classified into three groups, namely (a) amino acid type, (b) imidazoline and lecithin amphoterics and (c) pseudoamphoterics and miscellaneous amphoterics.

(a) Amino Acid Type Amphoterics

Amphoteric compounds of amino acid type include all the amino acids, dipeptides, polypeptides, proteins and the like which contain at least one of the basic groups such as amino, imino, guanido, imidazolino and imidazolyl, and one of the acidic groups such as carboxylic, sulfonic, sulfinic and sulfate.

Glycine is a simple amphoteric compound which contains only one amino group and one carboxylic group. Lysine contains two amino groups and one carboxylic group. Aspartic acid contains one amino group and two carboxylic groups. Arginine contains one amino group, one guanido group and one carboxylic group. Histidine contains one amino group, one imidazolyl group and one carboxylic group. Taurine contains one amino group and one sulfonic group. Cysteine sulfinic acid contains one amino group, one carboxylic group and one sulfinic group. The amino group of an amphoteric compound may also be substituted, such as in betaine which is a glycine N,N,N-trimethyl inner salt.

Glycylglycine is a simple dipeptide which contains one free amino group and one free carboxylic group. Glycylhistidine is also a dipeptide which contains one free amino group, one imidazolyl group and one free carboxylic group.

The representative amphoteric compounds of amino acid type may be listed as follows: Glycine, alanine, valine, leucine, isoleucine, serine, threonine, cysteine, cystine, methionine, aspartic acid, asparagine, glutamic acid, glutamine, arginine, lysine, 5-hydroxylysine, histidine, phenylalanine, tyrosine, tryptophan, 3-hydroxyproline, 4-hydroxyproline and proline.

The related amino acids include homocysteine, homocystine, homoserine, ornithine, citrulline, creatine, 3-aminopropanoic acid, theanine, 2-aminobutanoic acid, 4-aminobutanoic acid, 2-amino-2-methylpropanoic acid, 2-methyl-3-aminopropanoic acid, 2,6-diaminopimelic acid, 2-amino-3-phenylbutanoic acid, phenylglycine, canavanine, canaline, 4-hydroxyarginine, 4-hydroxyornithine, homoarginine, 4-hydroxyhomoarginine, β-lysine, 2,4-diaminobutanoic acid, 2,3-diaminopropanoic acid, 2-methylserine, 3-phenylserine and betaine.

Sulfur-containing amino acids include taurine, cysteinesulfinic acid, methionine sulfoxide and methionine sulfone.

The halogen-containing amino acids include 3,5-diiodotyrosine, thyroxine and monoiodotyrosine. The imino type acids include pipecolic acid, 4-aminopipecolic acid and 4-methylproline.

The dipeptides include for example, glycylglycine, carnosine, anserine, ophidine, homocarnosine, β-alanyllysine, β-alanylarginine. The tripeptides include for example, glutathione, ophthalmic acid and norophthalmic acid. Short-chain polypeptides of animal, plant and bacterial origin containing up to 100 amino acid residues include bradykinin and glucagon. The preferred proteins include for example protamines, histones and other lysine and arginine rich proteins.

(b) Imidazoline and Lecithin Amphoterics

The amphoteric compounds of imidazoline derived type are commercially synthesized from 2-substituted-2-imidazolines obtained by reacting a fatty acid with an aminoethylethanolamine. These amphoterics include cocoamphoglycine, cocoamphopropionate, and cocoamphopropylsulfonate. The amphoteric compounds of lecithin and related type include for example, phosphatidyl ethanolamine, phosphatidyl serine and sphingomyelin.

(c) Pseudoamphoterics and Miscellaneous Amphoterics

Many pseudoamphoteric compounds are chemically related or derived from true amphoterics. For example, creatinine is derived from creatine. Other pseudoamphoteric compounds may include fatty amide amines such as stearamidoethyl diethylamine, stearamidoethyl diethanolamine and stearamidopropyl dimethylamine. Other pseudoamphoteric related compounds include quaternary ammonium hydroxide and quaternium hydroxide.

In accordance with the present invention, the alpha hydroxyacid, the alpha ketoacids and the related compounds which are incorporated into amphoteric or pseudoamphoteric compositions for cosmetic conditions and dermatologic disorders may be classified into three groups.

The first group is organic carboxylic acids in which one hydroxyl group is attached to the alpha carbon of the acids. The generic structure of such alpha hydroxyacids may be represented as follows:

(Ra)(Rb)C(OH)COOH where Ra and Rb are H, F, Cl, Br, alkyl, aralkyl or aryl group of saturated or unsaturated, isomeric or non-isomeric, straight or branched chain or cyclic form, having 1 to 25 carbon atoms, and in addition Ra and Rb may carry OH, CHO, COOH and alkoxy group having 1 to 9 carbon atoms. The alpha hydroxyacids may be present as a free acid or lactone form, or in a salt form with an organic base or an inorganic alkali. The alpha hydroxyacids may exist as stereoisomers as D, L, and DL forms when Ra and Rb are not identical.

Typical alkyl, aralkyl and aryl groups for Ra and Rb include methyl, ethyl, propyl, isopropyl, butyl, pentyl, octyl, lauryl, stearyl, benzyl and phenyl, etc. The alpha hydroxyacids of the first group may be divided into (1) alkyl alpha hydroxyacids, (2) aralkyl and aryl alpha hydroxyacids, (3) polyhydroxy alpha hydroxyacids, and (4) polycarboxylic alpha hydroxyacids. The following are representative alpha hydroxyacids in each subgroup.

(1) Alkyl Alpha Hydroxyacids
1. 2-Hydroxyethanoic acid (Glycolic acid, hydroxyacetic acid)
   (H) (H) C (OH) COOH
2. 2-Hydroxypropanoic acid (Lactic acid)
   ($CH_3$) (H) C (OH) COOH
3. 2-Methyl 2-hydroxypropanoic acid (Methyllactic acid)
   ($CH_3$) ($CH_3$) C (OH) COOH
4. 2-Hydroxybutanoic acid
   ($C_2H_5$) (H) C (OH) COOH
5. 2-Hydroxypentanoic acid
   ($C_3H_7$) (H) C (OH) COOH
6. 2-Hydroxyhexanoic acid
   ($C_4H_9$) (H) C (OH) COOH
7. 2-Hydroxyheptanoic acid
   ($C_5H_{11}$) (H) C (OH) COOH
8. 2-Hydroxyoctanoic acid
   ($C_6H_{13}$) (H) C (OH) COOH
9. 2-Hydroxynonanoic acid
   ($C_7H_{15}$) (H) C (OH) COOH
10. 2-Hydroxydecanoic acid
    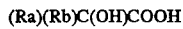$C_8H_{17}$) (H) C (OH) COOH
11. 2-Hydroxyundecanoic acid
    ($C_9H_{19}$) (H) C (OH) COOH
12. 2-Hydroxydodecanoic acid (Alpha hydroxylauric acid)
    ($C_{10}H_{21}$) (H) C (OH) COOH
13. 2-Hydroxytetradecanoic acid (Alpha hydroxymyristic acid)
    ($C_{12}H_{25}$) (H) C (OH) COOH
14. 2-Hydroxyhexadecanoic acid (Alpha hydroxypalmitic acid)
    $C_{14}H_{29}$) (H) C (OH) COOH
15. 2-Hydroxyoctadecanoic acid (Alpha hydroxystearic acid)
    ($C_{16}H_{34}$) (H) C (OH) COOH
16. 2-Hydroxyeicosanoic acid (Alpha hydroxyarachidonic acid)
    ($C_{18}H_{37}$) (H) C (OH) COOH (2) Aralkyl and Aryl Alpha Hydroxyacids
1. 2-Phenyl 2-hydroxyethanoic acid (Mandelic acid)
   ($C_6H_5$) (H) C (OH) COOH
2. 2,2-Diphenyl 2-hydroxyethanoic acid (Benzilic acid)
   ($C_6H_5$) ($C_6H_5$) C (OH) COOH
3. 3-Phenyl 2-hydroxypropanoic acid (Phenyllactic acid)
   ($C_6H_5CH_2$) (H) C (OH) COOH
4. 2-Phenyl 2-methyl 2-hydroxyethanoic acid (Atrolactic acid)
   ($C_6H_5$) ($CH_3$) C (OH) COOH
5. 2-(4'-Hydroxyphenyl) 2-hydroxyethanoic acid (4-Hydroxymandelic acid)
   (HO—$C_6H_4$) (H) C (OH) COOH
6. 2-(4'-Chlorophenyl) 2-hydroxyethanoic acid (4-Chloromandelic acid)
   (Cl—$C_6H_4$) (H) C (OH) COOH
7. 2-(3'-Hydroxy-4'-methoxyphenyl) 2-hydroxyethanoic acid (3-Hydroxy-4-methoxymandelic acid)
   (HO—,$CH_3O$—$C_6H_3$) (H) C (OH) COOH
8. 2-(4'-Hydroxy-3'-methoxyphenyl) 2-hydroxyethanoic acid (4-Hydroxy-3-methoxymandelic acid)
   (HO—,$CH_3O$—$C_6H_3$) (H) C (OH) COOH
9. 3-(2'-Hydroxyphenyl) 2-hydroxypropanoic acid [3-(2'-Hydroxyphenyl) lactic acid]
   HO—$C_6H_4$—$CH_2$ (H) C (OH) COOH 10. 3-(4'-Hydroxyphenyl) 2-hydroxypropanoic acid [3-(4'-Hydroxyphenyl) lactic acid]

HO—$C_6H_4$—$CH_2$ (H) C (OH) COOH 11. 2-(3',4'-Dihydroxyphenyl) 2-hydroxyethanoic acid (3,4-Dihydroxymandelic acid)

HO—,HO—$C_6H_3$ (H) C (OH) COOH (3) Polyhydroxy Alpha Hydroxyacids 1. 2,3-Dihydroxypropanoic acid (Glyceric acid)

($HOCH_2$) (H) C (OH) COOH 2. 2,3,4-Trihydroxybutanoic acid (Isomers; erythronic acid, threonic acid)

$HOCH_2$ (HO)$CH_2$ (H) C (OH) COOH 3. 2,3,4,5-Tetrahydroxypentanoic acid (Isomers; ribonic acid, arabinoic acid, xylonic acid, lyxonic acid)

$HOCH_2$ (HO)$CH_2$ (HO)$CH_2$ (H) C (OH) COOH 4. 2,3,4,5,6-Pentahydroxyhexanoic acid (Isomers; allonic acid, altronic acid, gluconic acid, mannoic acid, gulonic acid, idonic acid, galactonic acid, talonic acid)

$HOCH_2$ (HO)$CH_2$ (HO)$CH_2$ (HO)$CH_2$ (H) C (OH) COOH 5. 2,3,4,5,6,7-Hexahydroxyheptanoic acid (Isomers; glucoheptonic acid, galactoheptonic acid etc.)

$HOCH_2$ (HO) $CH_2$ (HO)$CH_2$ (HO) $CH_2$ (HO) $CH_2$ (H) C (OH) COOH (4) Polycarboxylic Alpha Hydroxyacids 1. 2-Hydroxypropane-1,3-dioic acid (Tartronic acid)

HOOC (H) C (OH) COOH 2. 2-Hydroxybutane-1,4-dioic acid (Malic acid)

HOOC $CH_2$ (H) C (OH) COOH 3. 2,3-Dihydroxybutane-1,4-dioic acid (Tartaric acid)

HOOC (HO)CH (H) C (OH) COOH 4. 2-Hydroxy-2-carboxypentane-1,5-dioic acid (Citric acid)

HOOC $CH_2$ C (OH)(COOH) $CH_2$ COOH 5. 2,3,4,5-Tetrahydroxyhexane-1,6-dioic acid (Isomers; saccharic acid, mucic acid etc.)

HOOC (CHOH)$_4$ COOH (5) Lactone Forms

The typical lactone forms are gluconolactone, galactonolactone, glucuronolactone, galacturonolactone, gulonolactone, ribonolactone, saccharic acid lactone, pantoyllactone, glucoheptonolactone, mannonolactone, and galactoheptonolactone.

The second group Of compounds which may be incorporated into amphoteric or pseudoamphoteric compositions for cosmetic conditions and dermatologic disorders, is organic carboxylic acids in which the alpha carbon of the acids is in keto form. The generic structure of such alpha ketoacids may be represented as follows:

(Ra)COCOO(Rb)

wherein Ra and Rb are H, alkyl, aralkyl or aryl group of saturated or unsaturated, isomeric or non-isomeric, straight or branched chain or cyclic form, having 1 to 25 carbon atoms, and in addition Ra may carry F, Cl, Br, I, OH, CHO, COOH and alkoxy group having 1 to 9 carbon atoms. The alpha ketoacids may be present as a free acid or an ester form, or in a salt form with an organic base or an inorganic alkali. The typical alkyl, aralkyl and aryl groups for Ra and Rb include methyl, ethyl, propyl, isopropyl, butyl, pentyl, octyl, lauryl, stearyl, benzyl and phenyl, etc.

In contrast to alpha hydroxyacids the ester form of alpha ketoacids has been found to be therapeutically effective for cosmetic and dermatologic conditions and disorders. For example, while ethyl lactate has a minimal effect, ethyl pyruvate is therapeutically very effective. Although the real mechanism for such difference is not known, we have speculated that the ester form of an alpha ketoacid is chemically and/or biochemically very reactive, and a free acid form of the alpha ketoacid is released in the skin after the topical application.

The representative alpha ketoacids and their esters which may be useful in amphoteric or pseudoamphoteric compositions for cosmetic conditions and dermatologic disorders are listed below:

1. 2-Ketoethanoic acid (Glyoxylic acid)

(H) CO COOH

2. Methyl 2-ketoethanoate (H) CO $COOCH_3$ 3. 2-Ketopropanoic acid (Pyruvic acid)

$CH_3$ CO COOH

4. Methyl 2-ketopropanoate (Methyl pyruvate)

$CH_3$ CO $COOCH_3$

5. Ethyl 2-ketopropanoate (Ethyl pyruvate)

$CH_3$ CO $COOC_2H_5$

6. Propyl 2-ketopropanoate (Propyl pyruvate)

$CH_3$ CO $COOC_3H_7$ 7. 2-Phenyl-2-ketoethanoic acid (Benzoylformic acid)

$C_6H_5$ CO COOH

8. Methyl 2-phenyl-2-ketoethanoate (Methyl benzoylformate)

$C_6H_5$ CO $COOCH_3$

9. Ethyl 2-phenyl-2-ketoethanoate (Ethyl benzoylformate)

$C_6H_5$ CO $COOC_2H_5$ 10. 3-Phenyl-2-ketopropanoic acid (Phenylpyruvic acid)

$C_6H_5CH_2$ CO COOH

11. Methyl 3-phenyl-2-ketopropanoate (Methyl phenylpyruvate)

$C_6H_5CH_2$ CO $COOCH_3$

12. Ethyl 3-phenyl-2-ketopropanoate (Ethyl phenylpyruvate)

$C_6H_5CH_2$ CO $COOC_2H_5$ 13. 2-Ketobutanoic acid $C_2H_5$ CO COOH 14. 2-Ketopentanoic acid $C_3H_7$ CO COOH 15. 2-Ketohexanoic acid $C_4H_9$ CO COOH 16. 2-Ketoheptanoic acid $C_5H_{11}$ CO COOH 17. 2-Ketooctanoic acid $C_6H_{13}$ CO COOH 18. 2-Ketododecanoic acid $C_{10}H_{21}$ CO COOH 19. Methyl 2-ketooctanoate $C_6H_{13}$ CO $COOCH_3$ The third group of compounds which may be incorporated into amphoteric or pseudoamphoteric compositions for cosmetic and dermatologic conditions and disorders, is chemically related to alpha hydroxyacids or alpha ketoacids, and can be represented by their names instead of the above two generic structures. The third group of compounds include ascorbic acid, quinic acid, isocitric acid, tropic acid, trethocanic acid, 3-chlorolactic acid, cerebronic acid, citramalic acid, agaricic acid, 2-hydroxynervonic acid, aleuritic acid and pantoic acid.

II. Dimeric and Polymeric Forms of Hydroxyacids

When two or more molecules of hydroxycarboxylic acids either identical or non-identical compounds are reacted chemically to each other, dimeric or polymeric compounds will be formed. Such dimeric and polymeric compounds may be classified into three groups, namely (a) acyclic ester, (b) cyclic ester and (c) miscellaneous dimer and polymer.

(a) Acyclic Ester

The acyclic ester of a hydroxycarboxylic acid may be a dimer or a polymer. The dimer is formed from two molecules of a hydroxycarboxylic acid by reacting the carboxyl group of one molecule with the hydroxy group of a second molecule. For example, glycolyl glycollate is formed from two molecules of glycolic acid by eliminating one mole of water molecule. Likewise, lactyl lactate is formed from two molecules of lactic acid. When two molecules of different hydroxycarboxylic acids are intermolecularly reacted, a different dimer is formed. For example, glycolyl lactate is formed by reacting the carboxyl group of lactic acid with the hydroxy group of glycolic acid. The polymer is formed in a similar manner but from more than two molecules of a hydroxycarboxylic acid. For example, glycoly glycoly glycollate is formed from three molecules of glycolic acid. Copolymer is formed from two or more than two different kinds of hydroxycarboxylic acids. For example, glycolyl lactyl glycollate is formed from two molecules of glycolic acid and one molecule of lactic acid.

The acyclic ester of dimeric and polymeric hydroxycarboxylic acids may be shown by the following chemical structure:

wherein Ra,Rb=H, alkyl, aralkyl ar aryl group of saturated or unsaturated, isomeric or non-isomeric, straight or branched chain or cyclic form, having 1 to 25 carbon atoms, and n=1 or any numerical number, with a preferred number of up to 200. Ra and Rb in monomer unit 2, 3, 4 and so on may be the same or the different groups from that in monomer unit 1. For example, Ra,Rb=H in monomer unit 1, and Ra=$CH_3$, Rb=H in monomer unit 2 when n=2 is a dimer called lactyl glycollate, because the first monomer is glycollate unit and the second monomer is lactic acid unit. The hydrogen atom in Ra and Rb may be substituted by a halogen atom or a radical such as a lower alkyl, aralkyl, aryl or alkoxy of saturated or unsaturated, isomeric or non-isomeric, straight or branched chain or cyclic form, having 1 to 9 carbon atoms. The dimer and polymer of a hydroxycarboxylic acid may be present as a free acid, ester or salt form with organic base or inorganic alkali.

The typical alkyl, aralkyl and aryl groups for Ra and Rb include methyl, ethyl, propyl, isopropyl, butyl, benzyl and phenyl. Representative acyclic esters of hydroxycarboxylic acids which may be useful for cosmetic conditions and dermatologic disorders are listed below:

1. Glycolyl glycollate (Glycolic acid glycollate)
   Ra,Rb=H in units 1 & 2, n=2
2. Lactyl lactate (Lactic acid lactate)
   Ra=$CH_3$,Rb=H in units 1 & 2, n=2
3. Mandelyl mandellate
   Ra=$C_6H_5$,Rb=H in units 1 & 2, n=2
4. Atrolactyl atrolactate
   Ra=$C_6H_5$, Rb=$CH_3$ in units 1 & 2, n=2
5. Phenyllactyl phenyllactate
   Ra=$C_6H_5CH_2$, Rb=H, in units 1 & 2, n=2
6. Benzilyl benzillate
   Ra,Rb=$C_6H_5$ in units 1 & 2, n=2
7. Glycolyl lactate
   Ra=$CH_3$ in unit 1, Ra=H in unit 2, Rb=H in units 1 & 2, n=2

8. Lactyl glycollate
   Ra=H in unit 1, Ra=$CH_3$ in unit 2, Rb=H in units 1 & 2, n=2
9. Glycolyl glycolyl glycollate
   Ra,Rb=H in units 1, 2 & 3, n=3
10. Lactyl lactyl lactate
    Ra=$CH_3$, Rb=H in units 1, 2 & 3, n=3
11. Lactyl glycolyl lactate
    Ra=$CH_3$ in units 1 & 3, Ra=H in unit 2, Rb=H in units 1, 2 & 3, n=3
12. Glycolyl glycolyl glycolyl glycollate
    Ra,Rb=H in units 1, 2, 3 & 4, n=4
13. Lactyl lactyl lactyl lactate
    Ra=$CH_3$, Rb=H in units 1, 2, 3 & 4, n=4
14. Glycolyl lactyl glycolyl lactyl glycollate
    Ra=H in units 1, 3 & 5, Ra=$CH_3$ in units 2 & 4, Rb=H in units 1, 2, 3, 4 & 5, n=5
15. Polyglycolic acid and polylactic acid (b) Cyclic Ester The cyclic ester of a hydroxycarboxylic acid may also be a dimer or polymer, the most common type however, is a dimer form. The cyclic dimer may be formed from an identical monomer or different monomers. For example, glycolide is formed from two molecules of glycolic acid by removing two molecules of water, and lactide is formed from two molecules of lactic acid in the same manner. The cyclic ester of dimeric and polymeric hydroxycarboxylic acids may be shown by the following chemical structure:

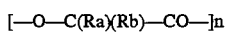

wherein Ra,Rb=H, alkyl, aralkyl or aryl group of saturated or unsaturated, isomeric or non-isomeric, straight or branched chain or cyclic form, having 1 to 25 carbon atoms, and n=1 or any numerical number, however with a preferred number of 2. Ra and Rb in units 1, 2, 3 and so on may be the same or the different groups. For example, in glycolide Ra and Rb are H in both units 1 & 2, but in lactoglycolide Ra is H in unit 1, $CH_3$ in unit 2 and Rb is H in both units 1 & 2. The hydrogen atom in Ra and Rb may be substituted by a halogen atom or a radical such as a lower alkyl, aralkyl, aryl or alkoxy of saturated or unsaturated, isomeric or non-isomeric, straight or branched chain or cyclic form, having 1 to 9 carbon atoms.

The typical alkyl, aralkyl and aryl groups for Ra and Rb include methyl, ethyl, propyl, isopropyl, butyl, benzyl and phenyl. Representative cyclic esters of hydroxycarboxylic acids which may be useful for cosmetic conditions and dermatologic disorders are listed below:

1. Glycolide
   Ra,Rb=H, n=2
2. Lactide
   Ra=$CH_3$, Rb=H in units 1 & 2, n=2
3. Mandelide
   Ra=$C_6H_5$, Rb=H in units 1 & 2, n=2
4. Atrolactide
   Ra=$C_6H_5$, Rb=$CH_3$ in units 1 & 2, n=2
5. Phenyllactide
   Ra=$C_6H_5 CH_2$, Rb=H in units 1 & 2, n=2
6. Benzilide
   Ra,Rb=$C_6H_5$ in units 1 & 2, n=2
7. Methyllactide
   Ra,Rb=$CH_3$ in units 1 & 2, n=2

8. Lactoglycolide
Ra=H in unit 1, Ra=CH₃ in unit 2
Rb=H in units 1 & 2, n=2
9. Glycolactide
Ra=CH₃ in unit 1, Ra=H in unit 2
Rb=H in units 1 & 2, n=2

(c) Miscellaneous Dimer and Polymer

This group includes all the dimeric and polymeric forms of hydroxycarboxylic acids, which can not be represented by any one of the above two generic structures, such as those formed from tropic acid, trethocanic acid and aleuritic acid. When a hydroxycarboxylic acid has more than one hydroxy or carboxy group in the molecule a complex polymer may be formed. Such complex polymer may consist of acyclic as well as cyclic structures.

The following hydroxycarboxylic acids have more than one hydroxy groups: glyceric acid, gluconic acid and gluconolactone, galactonic acid and galactonolactone, glucuronic acid and glucuronolactone, ribonic acid and ribonolactone, galacturonic acid and galacturonolactone, ascorbic acid, gulonic acid and gulonolactone, glucoheptonic acid and glucoheptonolactone. These polyhydroxycarboxylic acids can form complex polymers with themselves or with other simple monohydroxymonocarboxylic acids.

The following hydroxycarboxylic acids have more than one carboxyl groups: malic acid, citric acid, citramalic acid, tartronic acid, agaricic acid and isocitric acid. These monohydroxypolycarboxylic acids can also form complex polymers with themselves or with other simple hydroxycarboxylic acids.

The following hydroxycarboxylic acids have more than one hydroxy and more than one carboxyl groups: tartaric acid, mucic acid and saccharic acid. These polyhydroxypolycarboxylic acids can form even more complex polymers with themselves or with other hydroxycarboxylic acids.

III. Combination Compositions

Any cosmetic and pharmaceutical agents may be incorporated into amphoteric or pseudoamphoteric compositions, or into compositions containing dimeric or polymeric forms of hydroxyacids with or without amphoteric or pseudoamphoteric systems to enhance therapeutic effects of those cosmetic and pharmaceutical agents to improve cosmetic conditions or to alleviate the symptoms of dermatologic disorder. Cosmetic and pharmaceutical agents include those that improve or eradicate age spots, keratoses and wrinkles; analgesics; anesthetics; antiacne agents; antibacterials; antiyeast agents; antifungal agents; antiviral agents; antidandruff agents; antidermatitis agents; antipruritic agents; antiemetics; antimotion sickness agents; antiinflammatory agents; antihyperkeratolytic agents; antidryskin agents; antiperspirants; antipsoriatic agents; antiseborrheic agents; hair conditioners and hair treatment agents; antiaging and antiwrinkle agents; antiasthmatic agents and bronchodilators; sunscreen agents; antihistamine agents; skin lightening agents; depigmenting agents; vitamins; corticosteroids; tanning agents; hormones; retinoids; topical cardiovascular agents and other dermatologicals.

Some examples of cosmetic and pharmaceutical agents are clotrimazole, ketoconazole, miconazole, griseofulvin, hydroxyzine, diphenhydramine, pramoxine, lidocaine, procaine, mepivacaine, monobenzone, erythromycin, tetracycline, clindamycin, meclocycline, hydroquinone, minocycline, naproxen, ibuprofen, theophylline, cromolyn, albuterol, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, benzoyl peroxide, crotamiton, propranolol, promethazine, vitamin A palmitate and vitamin E acetate.

IV. Specific Compositions for Skin Disorders

We have discovered that topical formulations or compositions containing specific alpha hydroxyacids or alpha ketoacids, or related compounds are therapeutically very effective for certain skin disorders without utilizing any amphoteric or pseudoamphoteric systems. The alpha hydroxyacids and the related compounds include 2-hydroxyethanoic acid, 2-hydroxypropanoic acid, 2-methyl 2-hydroxypropanoic acid, 2-phenyl 2-hydroxyethanoic acid, 2,2-diphenyl 2-hydroxyethanoic acid, 2-phenyl 2-methyl 2-hydroxyethanoic acid and 2-phenyl 3-hydroxypropanoic acid. The alpha ketoacids and their esters include 2-ketopropanoic acid, methyl 2-ketopropanoate and ethyl 2-ketopropanoate. The mentioned skin disorders include warts, keratoses, age spots, acne, nail infections, wrinkles and aging related skin changes.

In general, the concentration of the alpha hydroxyacid, the alpha ketoacid or the related compound used in the composition is a full strength to an intermediate strength, therefore the dispensing and the application require special handling and procedures.

If the alpha hdyroxyacid, or the alpha ketoacid or the related compound at full strength (usually 95–100%) is a liquid form at room temperature such as 2-hydroxypropanoic acid, 2-ketopropanoic acid, methyl 2-ketopropanoate and ethyl 2-ketopropanoate, the liquid compound with or without a gelling agent is directly dispensed as 0.5 to 1 ml aliquots in small vials.

If the alpha hydroxyacid, or the alpha ketoacid or the related compound at full strength is a solid form at room temperature such as 2-hydroxyethanoic acid, 2-methyl 2-hydroxypropanoic acid, 2-phenyl 2-hydroxyethanoic acid, 2,2-diphenyl 2-hydroxyethanoic acid and 2-phenyl 3-hydroxypropanoic acid, the solid compound is first dissolved in a minimal amount of vehicle or vehicle system such as water, or ethanol and propylene glycol with or without a gelling agent. For example, 2-hydroxyethanoic acid 70 g is dissolved in water 30 g, and the 70% strength solution thus obtained is dispensed as 0.5 to 1 ml aliquots in small vials. If a gelling agent is used, 0.5 to 3% of for example, hydroxyethyl cellulose, methyl cellulose, hydroxypropyl cellulose or carbomer may be incorporated into the above solution.

To prepare an intermediate strength (usually 20–50%), the alpha hydroxyacid, alpha ketoacid or related compound either a liquid or solid form at room temperature is first dissolved in a vehicle or vehicle system such as water, acetone, ethanol, propylene glycol and butane 1,3-diol. For example, 2-hydroxyethanoic acid or 2-ketopropanoic acid 30 g is dissolved in ethanol 56 g and propylene glycol 14 g, and the 30% strength solution thus obtained is dispensed as 7 to 14 ml aliquots in dropper bottles.

For topical treatment of warts, keratoses, age spots, acne, nail infections, wrinkles or aging related skin changes, patients are advised to apply a small drop of the medication with a toothpick or a fine-caliber, commonly available artist's camel hair brush to affected lesions only and not surrounding skin. Prescribed applications have been 1 to 6 times daily for keratoses and ordinary warts of the hands, fingers, palms, and soles. For age spots, acne, nail infections, wrinkles and aging related skin changes topical applications have been 1 to 2 times daily.

Very often, frequency and duration of applications have been modified according to clinical responses and reactions of the lesions and the patient or responsible family member is instructed accordingly. For example, some clinical manifestations other than pain have been used as a signal to interrupt application. These manifestations include distinct blanching of the lesions or distinct peripheral erythema.

Alternatively, an office procedure may be adapted when a full strength of 2-ketopropanoic acid or 70% 2-hydroxyethanoic acid is used for topical treatment of age spots, keratoses, acne, warts or facial wrinkles.

We have found that the above mentioned alpha hydroxyacids, alpha ketoacids and related compounds are therapeutically effective for topical treatments of warts, keratoses, age spots, ache, nail infections, wrinkles and aging related skin changes.

Preparation of the Therapeutic Compositions

Amphoteric and pseudoamphoteric compositions of the instant invention may be formulated as solution, gel, lotion, cream, ointment, shampoo, spray, stick, powder or other cosmetic and pharmaceutical preparations.

To prepare an amphoteric or pseudoamphoteric composition in solution form at least one of the aforementioned amphoteric or pseudoamphoteric compounds and in combination at least one of the hydroxyacids or the related compounds are dissolved in a solution which may consist of ethanol, water, propylene glycol, acetone or other Pharmaceutically acceptable vehicle. The concentration of the amphoteric or pseudoamphoteric compound may range from 0.01 to 10M, the preferred concentration ranges from 0.1 to 3M. The concentration of hydroxyacids or the related compounds may range from 0.02 to 12M, the preferred concentration ranges from 0.2 to 5M.

In the preparation of an amphoteric or pseudoamphoteric composition in lotion, cream or ointment form, at least one of the amphoteric or pseudoamphoteric compounds and one of the hydroxyacids or the related compounds are initially dissolved in a solvent such as water, ethanol and/or propylene glycol. The solution thus prepared is then mixed in a conventional manner with commonly available cream or ointment base such as hydrophilic ointment or petrolatum. The concentrations of amphoteric or pseudoamphoteric compounds and hydroxyacids used in the compositions are the same as described above.

Amphoteric and pseudoamphoteric compositions of the instant invention may also be formulated in a gel form. A typical gel composition of the instant invention utilizes at least one of the amphoteric or pseudoamphoteric compounds and one of the hydroxyacids or the related compounds are dissolved in a mixture of ethanol, water and propylene glycol in a volume ratio of 40:40:20, respectively. A gelling agent such as methyl celluluose, ethyl cellulose, hydroxyethylcellulose, hydroxypropylcellulose, hydroxypropylmethylcellulose, carbomer or ammoniated glycyrrhizinate is then added to the mixture with agitation. The preferred concentration of the gelling agent may range from 0.1 to 4 percent by weight of the total composition.

Since dimeric and polymeric forms of hydroxyacids are less stable in the presence of water or the like vehicle, cosmetic and pharmaceutical compositions should be prepared as anhydrous formulations. Typical vehicles suitable for such formulations include mineral oil, petrolatum, isopropyl myristate, isopropyl palmitate, diisopropyl adipate, ocetyl palmitate, acetone, squalene, squalane, silicone oils, vegetable oils and the like. Therapeutic compositions containing dimeric or polymeric forms of hydroxyacids do not require any incorporation of an amphoteric or pseudoamphoteric compound. The concentration of the dimeric or polymeric form of a hydroxyacid used in the composition may range from 0.1 to 100%, the preferred concentration ranges from 1 to 40%. Therapeutic compositions may be formulated as anhydrous solution, lotion, ointment, spray, powder or the like.

To prepare a combination composition in a pharmaceutically acceptable vehicle, a cosmetic or pharmaceutical agent is incorporated into any one of the above composition by dissolving or mixing the agent into the formulation.

The following are illustrative examples of formulations and compositions according to this invention. Although the examples utilize only selected compounds and formulations, it should be understood that the following examples are illustrative and not limited. Therefore, any of the aforementioned amphoteric or pseudoamphoteric compounds, hydroxyacids, dimeric or polymeric forms of hydroxyacids may be substituted according to the teachings of this invention in the following examples.

EXAMPLE 1

An amphoteric composition containing 1M 2-hydroxyethanoic acid and 0.5M L-arginine in solution form for dandruff or dry skin may be formulated as follows.

2-Hydroxyethanoic acid (glycolic acid) 7.6 g is dissolved in water 60 ml and propylene glycol 20 ml. L-Arginine 8.7 g is added to the solution with stirring until all the crystals are dissolved. Ethanol is added to make a total volume of the solution to 100 ml. The amphoteric composition thus formulated has pH 3.0. An amphoteric composition formulated from 1M 2-hydroxyethanoic acid and 1M L-arginine has pH 6.3. The solution has pH 1.9 if no amphoteric compound is incorporated.

EXAMPLE 2

An amphoteric composition containing 1M 2-hydroxyethanoic acid and 0.5M L-lysine in a cream form for dry skin and other dermatologic and cosmetic conditions may be formulated as follows.

2-Hydroxyethanoic acid 7.6 g and L-lysine 7.3 g are dissolved in 30 ml of water, and the solution thus obtained is mixed with sufficient amount of an oil-in-water emulsion to make a total volume of 100 ml. The amphoteric composition thus formulated has pH 3.3.

EXAMPLE 3

An amphoteric composition containing 1M 2-hydroxyethanoic acid and 0.5M 4-aminobutanoic acid in lotion form for cosmetic and dermatologic conditions may be formulated as follows.

2-Hydroxyethanoic acid 7.6 g and 4-aminobutanoic acid 5.2 g are dissolved in water 30 ml, and the solution is mixed with 50 g of an oil-in-water emulsion. The lotion thus obtained is made up to 100 ml in volume with more oil-in-water emulsion. The amphoteric composition thus formulated has pH 3.1.

EXAMPLE 4

A pseudoamphoteric composition containing 1M 2-hydroxyethanoic acid and 0.5M creatinine in solution form for cosmetic conditions and dermatologic disorders may be formulated as follows.

2-Hydroxyethanoic acid 7.6 g is dissolved in water 70 ml and propylene glycol 10 ml. Creatinine 5.7 g is added to the solution with stirring until all the crystals are dissolved. More water is added to make a total volume of the solution to 100 ml. The pseudoamphoteric composition thus formulated has pH 3.2. The composition has pH 4.0 when 1M instead of 0.5M creatinine is incorporated into the formulation.

EXAMPLE 5

An amphoteric composition containing 1M 2-hydroxyethanoic acid and 0.5M L-histidine in a cream form for dermatologic and cosmetic conditions may be formulated as follows.

2-Hydroxyethanoic acid 7.6 g and L-histidine 7.8 g are dissolved in 25 ml of water, and the solution thus obtained is mixed with sufficient amount of an oil-in-water emulsion to make a total volume of 100 ml. The amphoteric composition thus formulated has pH 3.2.

EXAMPLE 6

An amphoteric composition containing 0.5M 2-hydroxyethanoic acid and 0.5M dipeptide of β-Ala-L-His for cosmetic and dermatologic conditions may be formulated as follows.

2-Hydroxyethanoic acid 3.8 g and L-carnosine (β-alanyl-L-histidine) 11.3 g are dissolved in water 40 ml and propylene glycol 20 ml. After all the crystals have been dissolved sufficient amount of ethanol is added to make a total volume of the solution to 100 ml. The amphoteric composition thus formulated has pH 4.5.

EXAMPLE 7

An amphoteric composition containing 0.5M 2-hydroxyethanoic acid and 0.5M cycloleucine for cosmetic and dermatologic conditions may be formulated as follows.

2-Hydroxyethanoic acid 3.8 g and 1-aminocyclopentane-1-carboxylic acid (cycloleucine) 6.5 g are dissolved in water 40 ml and propylene glycol 20 ml. After all the crystals have been dissolved sufficient amount of ethanol is added to make a total volume of the solution to 100 ml. The amphoteric composition thus formulated has pH 3.2.

EXAMPLE 8

A pseudoamphoteric composition containing 0.5M 2-hydroxyethanoic acid and 0.25M 1,12-diaminododecane for cosmetic and dermatologic conditions may be formulated as follows.

2-Hydroxyethanoic acid 3.8 g and 1.12-diaminododecane 5 g are dissolved in water 40 ml and propylene glycol 20 ml. After all the crystals have been dissolved sufficient amount of ethanol is added to make a total volume of the solution to 100 ml. The pseudoamphoteric composition thus formulated has pH 4.2.

EXAMPLE 9

An amphoteric composition containing 0.5M 2-hydroxyethanoic acid and 5% protamine for cosmetic and dermatologic conditions may be formulated as follows.

2-Hydroxyethanoic acid 3.8 g and protamine 5 g, isolated and purified from salmon sperm are dissolved in water 25 ml. The solution thus obtained is mixed with sufficient amount of an oil-in-water emulsion to make a total volume of 100 ml. The amphoteric composition thus formulated has pH 3.2.

EXAMPLE 10

An amphoteric composition containing 1M 2-hydroxypropanoic acid and 0.5M L-arginine in solution form for dandruff or dry skin may be formulated as follows.

2-Hydroxypropanoic acid (DL-lactic acid) USP grade 9.0 g is dissolved in water 60 ml and propylene glycol 20 ml. L-Arginine 8.7 g is added to the solution with stirring until all the crystals are dissolved. Ethanol is added to make a total volume of the solution to 100 ml. The amphoteric composition thus formulated has pH 3.1. An amphoteric composition formulated from 1M 2-hydroxypropanoic acid and 1M L-arginine has pH 6.9. The solution has pH 1.9 if no amphoteric compound is incorporated.

EXAMPLE 11

An amphoteric composition containing 1M 2-hydroxypropanoic acid and 0.5M L-lysine in a cream form for dry skin and other dermatologic and cosmetic conditions may be formulated as follows.

2-Hydroxypropanoic acid 9.0 g and L-lysine 7.3 g are dissolved in 30 ml of water, and the solution thus obtained is mixed with sufficient amount of an oil-in-water emulsion to make a total volume of 100 ml. The amphoteric composition thus formulated has pH 3.6. An amphoteric composition formulated from 1M 2-hydroxypropanoic acid and 1M L-lysine has pH 8.4.

EXAMPLE 12

An amphoteric composition containing 1M 2-hydroxypropanoic acid and 0.5M 4-aminobutanoic acid in lotion form for cosmetic and dermatologic conditions may be formulated as follows.

2-Hydroxypropanoic acid 9.0 g and 4-aminobutanoic acid 5.2 g are dissolved in water 30 ml, and the solution is mixed with 50 g of an oil-in-water emulsion. The lotion thus obtained is made up to 100 ml in volume with more oil-in-water emulsion. The amphoteric composition thus formulated has pH 3.0.

EXAMPLE 13

A pseudoamphoteric composition containing 1M 2-hydroxypropanoic acid and 0.5M creatinine in solution form for cosmetic conditions and dermatologic disorders may be formulated as follows.

2-Hydroxypropanoic acid 9.0 g is dissolved in water 70 ml and propylene glycol 10 ml. Creatinine 5.7 g is added to the solution with stirring until all the crystals are dissolved. More water is added to make a total volume of the solution to 100 ml. The pseudoamphoteric composition thus formulated has pH 3.3. The composition has pH 4.4 when 1M instead of 0.5M creatinine is incorporated into the formulation.

EXAMPLE 14

An amphoteric composition containing 1M 2-hydroxypropanoic acid and 1M L-histidine in a cream form for dermatologic and cosmetic conditions may be formulated as follows.

2-Hydroxypropanoic acid 9.0 g and L-histidine 15.5 g are dissolved in 35 ml of water, and the solution thus obtained is mixed with sufficient amount of an oil-in-water emulsion to make a total volume of 100 ml. The amphoteric composition thus formulated as pH 4.9.

EXAMPLE 15

An amphoteric composition containing 1M 2-hydroxypropanoic acid and 1M dipeptide of Gly—Gly for cosmetic and dermatologic conditions may be formulated as follows.

2-Hydroxypropanoic acid 9.0 g and glycylglycine 13.2 g are dissolved in water 40 ml and propylene glycol 20 ml. After all the crystals have been dissolved sufficient amount of ethanol is added to make a total volume of the solution to 100 ml. The amphoteric composition thus formulated has pH 3.0.

EXAMPLE 16

An amphoteric composition containing 1M 2-methyl-2-hydroxypropanoic acid and 0.5M L-arginine in solution form for dandruff or dry skin may be formulated as follows.

2-Methyl-2-hydroxypropanoic acid (methyllactic acid) 10.4 g is dissolved in water 60 ml and propylene glycol 20 ml. L-Arginine 8.7 g is added to the solution with stirring until all the crystals are dissolved. Ethanol is added to make a total volume of the solution to 100 ml. The amphoteric composition thus formulated has pH 3.3. An amphoteric composition formulated from 1M 2-methyl-2-hydroxypropanoic acid and 1M L-arginine has pH 6.5. The solution has pH 1.9 if no amphoteric compound is incorporated.

EXAMPLE 17

An amphoteric composition containing 1M 2-methyl-2-hydroxypropanoic acid and 0.5M 4-aminobutanoic acid in a cream form for dry skin and other dermatologic and cosmetic conditions may be formulated as follows.

2-Methyl-2-hydroxypropanoic acid 10.4 g and 4-aminobutanoic acid 5.2 g are dissolved in 30 ml of water, and the solution thus obtained is mixed with sufficient amount of an oil-in-water emulsion to make a total volume of 100 ml. The amphoteric composition thus formulated has pH 3.2.

EXAMPLE 18

An amphoteric composition containing 1M 2-methyl-2-hydroxypropanoic acid and 1M dipeptide of Gly—Gly in lotion form for cosmetic and dermatologic conditions may be formulated as follows.

2-Methyl-2-hydroxypropanoic acid 10.4 g and glycylglycine 13.2 g are dissolved in water 30 ml, and the solution is mixed with 50 g of an oil-in-water emulsion. The lotion thus obtained is made up to 100 ml in volume with more oil-in-water emulsion. The amphoteric composition thus formulated has pH 3.0.

EXAMPLE 19

A pseudoamphoteric composition containing 1M 2-methyl-2-hydroxypropanoic acid and 0.5M creatinine in solution form for cosmetic conditions and dermatologic disorders may be formulated as follows.

2-Methyl-2-hydroxypropanoic acid 10.4 g is dissolved in water 70 ml and propylene glycol 10 ml. Creatinine 5.7 g is added to the solution with stirring until all the crystals are dissolved. More water is added to make a total volume of the solution to 100 ml. The pseudoamphoteric composition thus formulated has pH 3.4. The composition has pH 4.4 when 1M instead of 0.5M creatinine is incorporated into the formulation.

EXAMPLE 20

An amphoteric composition containing 0.5M 2-phenyl-2-hydroxyethanoic acid and 0.5M L-histidine in a cream form for dermatologic and cosmetic conditions may be formulated as follows.

2-Phenyl 2-hydroxyethanoic acid (mandelic acid) 7.6 g and L-histidine 7.8 g are dissolved in 25 ml of water, and the solution thus obtained is mixed with sufficient amount of an oil-in-water emulsion to make a total volume of 100 ml. The amphoteric composition thus formulated has pH 5.0. The composition has pH 2.2 if no amphoteric compound is incorporated.

EXAMPLE 21

An amphoteric composition containing 0.5M 2-phenyl-2-hydroxyethanoic acid and 0.5M L-lysine for cosmetic and dermatologic conditions may be formulated as follows.

2-Phenyl 2-hydroxyethanoic acid 7.6 g and L-lysine 7.3 g are dissolved in 25 ml of water. The solution thus obtained is mixed with an oil-in-water emulsion to make a total volume of 100 ml. The amphoteric composition thus formulated for pH 4.6.

EXAMPLE 22

A pseudoamphoteric composition containing 0.5M 2-phenyl 2-hydroxyethanoic acid and 0.5M creatinine for cosmetic and dermatologic conditions may be formulated as follows.

2-Phenyl 2-hydroxyethanoic acid 7.6 g and creatinine 5.7 g are dissolved in 30 ml of water, and the solution thus obtained is mixed with sufficient amount of an oil-in-water emulsion to make a total volume of 100 ml. The amphoteric composition thus formulated has pH 4.6.

EXAMPLE 23

An amphoteric composition containing 0.5M 2-phenyl 2-hydroxyethanoic acid and 0.5M L-citrulline for cosmetic and dermatologic conditions may be formulated as follows.

2-Phenyl 2-hydroxyethanoic acid 7.6 g and L-citrulline 8.8 g are dissolved in water 30 ml, and the solution is mixed with 50 g of an oil-in-water emulsion. The lotion thus obtained is made up to 100 ml in volume with more oil-in-water emulsion. The amphoteric composition thus formulated has pH 3.0.

EXAMPLE 24

An amphoteric composition containing 1M citric acid and 1M L-arginine for cosmetic conditions and dermatologic disorders may be formulated as follows.

Citric acid 19.2 g is dissolved in water 50 ml and propylene glycol 10 ml. L-Arginine 17.4 g is added to the solution with stirring until all the crystals are dissolved. More water is added to make a total volume of the solution to 100 ml. The amphoteric composition thus formulated has pH 3.0. The composition has pH 1.8 if no amphoteric compound is incorporated.

EXAMPLE 25

A pseudoamphoteric composition containing 1M citric acid and 1M creatinine for dermatologic and cosmetic conditions may be formulated as follows.

Citric acid 19.2 g and creatinine 11.3 g are dissolved in 40 ml of water, and the solution thus obtained is mixed with sufficient amount of an oil-in-water emulsion to make a total volume of 100 ml. The amphoteric composition thus formulated has pH 3.7.

EXAMPLE 26

An amphoteric composition containing 1M malic acid and 1M L-arginine for cosmetic and dermatologic conditions may be formulated as follows.

2-Hydroxybutanedioic acid (DL-malic acid) 13.4 g and L-arginine 17.4 g are dissolved in water 40 ml and propylene glycol 20 ml. After all the crystals have been dissolved sufficient amount of water is added to make a total volume of the solution to 100 ml. The amphoteric composition thus formulated has pH 3.3. The composition has pH 1.8 if no amphoteric compound is incorporated.

EXAMPLE 27

A pseudoamphoteric composition containing 1M malic acid and 0.5M creatinine for cosmetic and dermatologic conditions may be formulated as follows.

DL-Malic acid 13.4 g and creatinine 5.7 g are dissolved in water 40 ml and propylene glycol 20 ml. After all the crystals have been dissolved sufficient amount of water is added to make a total volume of the solution to 100 ml. The pseudoamphoteric composition thus formulated has pH 3.0. The composition has pH 3.8 when 1M instead of 0.5M creatinine is incorporated into the formulation.

EXAMPLE 28

An amphoteric composition containing 1M tartaric acid and 1M L-arginine for cosmetic and dermatologic conditions may be formulated as follows.

2,3-Dihydroxybutanedioic acid (DL-tartaric acid) 15.9 g and L-arginine 17.4 g are dissolved in water 40 ml and propylene glycol 20 ml. After all the crystals have been dissolved sufficient amount of water is added to make a total volume of the solution to 100 ml. The amphoteric composition thus formulated has pH 3.0. The composition has pH 1.7 if no amphoteric compound is incorporated.

EXAMPLE 29

A pseudoamphoteric composition containing 1M tartaric acid and 1M creatinine for cosmetic and dermatologic conditions may be formulated as follows.

DL-Tartaric acid 15.0 g and creatinine 11.3 g are dissolved in 35 ml of water. The solution thus obtained is mixed with sufficient amount of an oil-in-water emulsion to make a total volume of 100 ml. The pseudoamphoteric composition thus formulated has pH 3.4.

EXAMPLE 30

An amphoteric composition containing 1M gluconolactone and 0.5M L-arginine for cosmetic and dermatologic conditions may be formulated as follows.

Gluconolactone 17.8 g and L-arginine 8.7 g are dissolved in water 60 ml and propylene glycol 10 ml. After all the crystals have been dissolved sufficient water is added to make a total volume of the solution to 100 ml. The amphoteric composition thus formulated has pH 3.1. The composition has pH 5.9 when 1M instead of 0.5M L-arginine is incorporated into the formulation. If no amphoteric compound is incorporated the pH of the composition is 1.8.

EXAMPLE 31

An amphoteric composition containing 1M gluconolactone and 0.5M 4-aminobutanoic acid for cosmetic and dermatologic conditions may be formulated as follows.

Gluconolactone 17.8 g and 4-aminobutanoic acid 5.2 g are dissolved in water 60 ml and propylene glycol 10 ml. After all the crystals have been dissolved sufficient water is added to make a total volume of the solution to 100 ml. The amphoteric composition thus formulated has pH 3.2.

EXAMPLE 32

An amphoteric composition containing 1M gluconolactone and 1M dipeptide of Gly—Gly for cosmetic and dermatologic conditions may be formulated as follows.

Gluconolactone 17.8 g and glycylglycine 13.2 g are dissolved in water 50 ml and propylene glycol 5 ml. More water is added to make a total volume of the solution to 100 ml. The amphoteric composition thus formulated has pH 3.1

EXAMPLE 33

A pseudoamphoteric composition containing 1M gluconolactone and 0.5M creatinine for cosmetic conditions and dermatologic disorders may be formulated as follows.

Gluconolactone 17.8 g and creatinine 5.7 g are dissolved in water 60 ml and propylene glycol 10 ml. More water is added to make a total volume of the solution to 100 ml. The pseudoamphoteric composition thus formulated has pH 3.2. The composition has pH 4.8 when 1M instead of 0.5M creatinine is incorporated into the formulation.

EXAMPLE 34

A pseudoamphoteric composition containing 1M pyruvic acid and 1M creatinine for dermatologic and cosmetic conditions may be formulated as follows.

2-Ketopropanoic acid (pyruvic acid) 8.8 g and creatinine 11.3 g are dissolved in water 25 ml. The solution thus obtained is mixed with sufficient amount of an oil-in-water emulsion to make a total volume of 100 ml. The amphoteric composition thus formulated has pH 3.4.

EXAMPLE 35

An amphoteric composition containing 0.5M benzilic acid and 0.5M L-lysine for cosmetic and dermatologic conditions may be formulated as follows.

2,2-Diphenyl 2-hydroxyethanoic acid (benzilic acid) 11.4 g and L-lysine 7.3 g are dissolved in water 40 ml and propylene glycol 20 ml. After all the crystals have been dissolved sufficient amount of ethanol is added to make a total volume of the solution to 100 ml. The amphoteric composition thus formulated has pH 4.9. The composition has pH 2.7 if no amphoteric compound is incorporated.

EXAMPLE 36

An amphoteric composition containing 0.5M benzilic acid and 0.5M L-histidine for cosmetic and dermatologic conditions may be formulated as follows.

Benzilic acid 11.4 g and L-histidine 7.8 g are dissolved in water 40 ml and propylene glycol 20 ml. Ethyl cellulose 2 g is added with stirring, and sufficient amount of ethanol is added to make a total volume of the gel to 100 ml. The amphoteric gel composition thus formulated has pH 5.0.

EXAMPLE 37

A pseudoamphoteric composition containing 0.5M benzilic acid and 0.5M creatinine for cosmetic and dermatologic conditions may be formulated as follows.

Benzilic acid 11.4 g and creatinine 5.7 g are dissolved in water 40 ml and propylene glycol 20 ml. Sufficient amount of ethanol is added to make a total volume of the solution to 100 ml. The amphoteric composition thus formulated has pH 4.9.

EXAMPLE 38

A pseudoamphoteric composition containing in combination 0.5M 2-hydroxyethanoic acid and 0.05% betamethasone dipropionate in a cream form for dermatologic disorders may be formulated as follows.

2-Hydroxyethanoic acid 3.8 g and creatinine 5.7 g are dissolved in 25 ml of water, and the solution thus obtained is mixed with 50 g of an oil-in-water emulsion. Betamethasone dipropionate 1% in ethanol solution 5 ml is added to the above mixture. More oil-in-water emulsion is added to make a total volume of 100 ml. The pseudoamphoteric composition thus formulated has pH 4.2.

EXAMPLE 39

A pseudoamphoteric composition containing in combination 0.5M 2-hydroxyethanoic acid and 0.05% clobetasol propionate in a cream form for dermatologic disorders may be formulated as follows.

2-Hydroxyethanoic acid 3.8 g and creatinine 5.7 g are dissolved in 25 ml of water, and the solution thus obtained is mixed with 50 g of an oil-in-water emulsion. Clobetasol propionate 1% in acetone solution 5 ml is added to the above mixture. More oil-in-water emulsion is added to make a total volume of 100 ml. The pseudoamphoteric composition thus formulated has pH 4.2.

EXAMPLE 40

A pseudoamphoteric composition containing in combination 0.5M 2-hydroxyethanoic acid and 0.1% triamcinolone acetonide in a cream form for dermatologic disorders may be formulated as follows.

2-Hydroxyethanoic acid 3.8 g and creatinine 5.7 g are dissolved in 25 ml of water, and the solution thus obtained is mixed with 50 g of an oil-in-water emulsion. Triamcinolone acetonide 2% solution of acetone:ethanol (50:50), 5 ml is added to the above mixture. More oil-in-water emulsion is added to make a total volume of 100 ml. The pseudoamphoteric composition thus formulated has pH 4.2.

EXAMPLE 41

A pseudoamphoteric composition containing in combination 0.5M 2-hydroxyethanoic acid and 0.2% 5-fluorouracil in a cream form for dermatologic disorders may be formulated as follows.

2-Hydroxyethanoic acid 3.8 g and creatinine 5.7 g are dissolved in 20 ml of water, and the solution thus obtained is mixed with 50 g of an oil-in-water emulsion. 5-Fluorouracil 2% solution of propylene glycol: water (95:5), 10 ml is added to the above mixture. More oil-in-water emulsion is added to make a total volume of 100 ml. The pseudoamphoteric composition thus formulated has pH 4.1.

EXAMPLE 42

A pseudoamphoteric composition containing in combination 0.5M 2-hydroxypropanoic acid and 0.05% betamethasone dipropionate in a cream form for dermatologic disorders may be formulated as follows.

2-Hydroxypropanoic acid 4.5 g and creatinine 5.7 g are dissolved in 25 ml of water, and the solution thus obtained is mixed with 50 g of a oil-in-water emulsion. Betamethasone dipropionate 1% in ethanol solution 5 ml is added to the above mixture. More oil-in-water emulsion is added to make a total volume of 100 ml. The pseudoamphoteric composition thus formulated has pH 4.1.

EXAMPLE 43

A pseudoamphoteric composition containing in combination 0.5M hydroxypropanoic acid and 0.05% clobetasol propionate in a cream form for dermatologic disorders may be formulated as follows.

2-Hydroxypropanoic acid 4.5 g and creatinine 5.7 g are dissolved in 25 ml of water, and the solution thus obtained is mixed with 50 g of an oil-in-water emulsion. Clobetasol propionate 1% in acetone solution 5 ml is added to the above mixture. More oil-in-water emulsion is added to make a total volume of 100 ml. The pseudoamphoteric composition thus formulated has pH 4.1.

EXAMPLE 44

A pseudoamphoteric composition containing in combination 0.5M 2-hydroxypropanoic acid and 0.1% triamcinolone acetonide in a cream form for dermatologic disorders may be formulated as follows.

2-Hydroxypropanoic acid 4.5 g and creatinine 5.7 g are dissolved in 25 ml of water, and the solution thus obtained is mixed with 50 g of an oil-in-water emulsion. Triamcinolone acetonide 2% solution of acetone:ethanol (50:50), 5 ml is added to the above mixture. More oil-in-water emulsion is added to make a total volume of 100 ml. The pseudoamphoteric composition thus formulated has pH 4.1.

EXAMPLE 45

A pseudoamphoteric composition containing in combination 0.5M 2-hydroxypropanoic acid and 0.2% 5-fluorouracil in a cream form for dermatologic disorders may be formulated as follows.

2-Hydroxypropanoic acid 4.5 g and creatinine 5.7 g are dissolved in 20 ml of water, and the solution thus obtained is mixed with 50 g of an oil-in-water emulsion. 5-Fluorouracil 2% solution of propylene glycol:water (95:5), 10 ml is added to the above mixture. More oil-in-water emulsion is added to make a total volume of 100 ml. The pseudoamphoteric composition thus formulated has pH 4.1.

EXAMPLE 46

A pseudoamphoteric composition containing in combination 0.5M 2-hydroxyethanoic acid and 2% clotrimazole in a cream form for athlete's foot and other fungal infections may be formulated as follows.

2-Hydroxyethanoic acid 3.8 g, clotimazole 2 g and creatinine 5.7 g are dissolved in water 20 ml and propylene glycol 5 ml, and the solution thus obtained is mixed with enough amount of an oil-in-water emulsion to make a total volume of 100 ml. The pseudoamphoteric composition thus formulated has pH 4.2.

EXAMPLE 47

A pseudoamphoteric composition containing in combination 0.5M 2-hydroxyethanoic acid and 2% erythromycin in solution form for acne may be formulated as follows.

2-Hydroxyethanoic acid 3.8 g, erythromycin 2 g and creatinine 5.7 g are dissolved in water 25 ml, ethanol 40 ml and propylene glycol 15 ml. More water is then added to make a total volume of 100 ml. The pseudoamphoteric composition thus formulated has pH 4.2.

EXAMPLE 48

A pseudoamphoteric composition containing in combination 0.5M 2-hydroxyethanoic acid and 1% ketoconazole in a cream form for fungal infections may be formulated as follows.

2-Hydroxyethanoic acid 3.8 g, ketoconazole 1 g and creatinine 5.7 g are dissolved in 25 ml of water, and the solution thus obtained is mixed with enough amount of an oil-in-water emulsion to make a total volume of 100 ml. The pseudoamphoteric composition thus formulated has pH 4.2.

EXAMPLE 49

A pseudoamphoteric composition containing in combination 0.5M 2-hydroxypropanoic acid and 2% clotrimazole in a cream form for fungal infections may be formulated as follows.

2-Hydroxypropanoic acid 3.8 g, clotrimazole 2 g and creatinine 5.7 g are dissolved in 25 ml of water, and the solution thus obtained is mixed with enough amount of an oil-in-water emulsion to make a total volume of 100 ml. The pseudoamphoteric composition thus formulated has pH 4.1.

EXAMPLE 50

A pseudoamphoteric composition containing in combination 0.5M 2-hydroxyethanoic acid and 2% tetracycline in a gel form for dermatologic disorders may be formulated as follows.

2-Hydroxyethanoic acid 3.8 g, tetracycline 2 g, creatinine 5.7 g, xantham gum 0.2 g, carbomer-941 1 g, propylene glycol 5 ml, ethanol 20 ml and enough amount of water are homogenized to make a total volume of 100 ml. The pseudoamphoteric composition thus formulated for acne and oily skin has pH 4.2.

EXAMPLE 51

An amphoteric composition containing 0.2M aleuritic acid and 0.1M L-lysine in a solution form for cosmetic and dermatologic conditions may be formulated as follows.

Aleuritic acid 6.1 g and L-lysine 1.5 g are dissolved in sufficient amount of a solution from ethanol:propylene glycol 80:20 to make a total volume of 100 ml. The amphoteric composition thus formulated has pH 6.4.

EXAMPLE 52

A typical composition containing a dimeric form of alpha hydroxyacid in solution for acne, dandruff, and as a skin cleanser may be formulated as follows.

Glycolide powder 1.0 g is dissolved in ethanol 89 ml and propylene glycol 10 ml. The composition thus formulated has pH 4.0, and contains 1% active ingredient.

EXAMPLE 53

A typical composition containing a dimeric form of alpha hdyroxyacid in ointment for dry skin, psoriasis, eczema, pruritus, wrinkles and other skin changes associated with aging may be formulated as follows.

Glycolide powder 2.0 g is mixed uniformly with petrolatum 66 g and mineral oil 32 g. The composition thus formulated contains 2% active ingredient.

EXAMPLE 54

A typical composition containing a full strength or a high concentration of an alpha hydroxyacid, alpha ketoacid or closely related compound for topical treatments of warts, keratoses, ache, age spots, nail infections, wrinkles and aging related skin changes may be prepared as follows.

If the alpha hydroxyacid, alpha ketoacid or closely related compound at full strength is a liquid form at room temperature such as 2-hydroxypropanoic acid, 2-ketopropanoic acid, methyl 2-ketopropanoate and ethyl 2-ketopropanoate, the compound is directly dispensed as 0.5 to 1 ml aliquots in small vials. If the compound is a solid form at room temperature such as 2-hydroxyethanoic acid and 2-methyl 2-hydroxypropanoic acid, it is first dissolved in minimal amount of an appropriate solvent or solvent system such as water or ethanol and propylene glycol with or without a gelling agent. For example, 2-hydroxyethanoic acid 70 g is dissolved in water 30 ml, and the 70% strength 2-hydroxyethanoic acid thus obtained is dispensed as 0.5 to 1 ml aliquots in small vials. If a gelling agent is used, methyl cellulose or hydroxyethyl cellulose 1 g may be added to the above solution.

EXAMPLE 55

A typical composition containing an intermediate strength of an alpha hydroxyacid, alpha ketoacid or closely related compound for topical treatment of warts, keratoses, acne, nail infections, age spots, wrinkles and aging related skin changes may be prepared as follows.

2-Hydroxyethanoic acid or 2-ketopropanoic acid 40 g is dissolved in ethanol 54 g and propylene glycol 6 g, and the 40% strength solution thus obtained is dispensed as 5 to 10 ml aliquots in dropper bottles.

TEST RESULTS

In order to determine whether amphoteric and pseudoamphoteric compositions of the instant invention were therapeutically effective for various cosmetic conditions and dermatologic disorders, a total of more than 90 volunteers and patients participated in these studies. Some participating subjects were given two preparations; an amphoteric or pseudoamphoteric composition containing an alpha hydroxyacid or the related compound, and a vehicle placebo. Others were given multiple preparations containing a known pharmaceutical agent such as a corticosteroid with or without incorporation of an amphoteric or pseudoamphoteric composition consisting of an alpha hydroxyacid or the related compound of the instant invention. The amphoteric and pseudoamphoteric compositions were formulated according to the Examples described in the previous section.

1. Common Dry Skin

Human subjects having ordinary dry skin or with moderate degrees of dry skin as evidenced by dryness, flaking and cracking of the skin were instructed to apply topically the lotion, cream or ointment containing an alpha hydroxyacid or the related compound in amphoteric or pseudoamphoteric composition, on the affected area of the skin. Topical application, two to three times daily, was continued for two to four weeks.

In all the 28 subjects tested, the feeling of the skin dryness disappeared within a week of topical application. The rough and cracked skin became less pronounced and the skin appeared normal and felt smooth after several days of topical treatment. The alpha hydroxyacids and the related compounds which have been found to be therapeutically effective when incorporated into the amphoteric or pseudo-amphoteric compositions for dry skin are as follows:

2-hydroxyethanoic acid (glycolic acid), 2-hydroxypropanoic acid (lactic acid), 2-methyl-2-hydroxypropanoic acid (methyllactic acid), phenyl 2-hydroxyethanoic acid (mandelic acid), phenyl 2-methyl-2-hydroxyethanoic acid (atrolactic acid), 3-phenyl-2-hydroxypropanoic acid (phenyllactic acid), diphenyl 2-hydroxyethanoic acid (benzilic acid), gluconolactone, tartaric acid, citric acid, saccharic acid, malic acid, tropic acid, glucuronic acid, galacturonic acid, gluconic acid, 3-hydroxybutanoic acid, quinic acid, ribonolactone, glucuronolactone, galactonolactone, pyruvic acid, methyl pyruvate, ethyl pyruvate, phenylpyruvic acid, benzoylformic acid and methyl benzoylformate.

The ordinary dry skin conditions, once restored to normal appearing skin, remained improved for some time until causes of dry skin, such as low humidity, cold weather, excessive contact pressure, detergents, soaps, solvents, chemicals, etc., again caused recurrence of the dry skin condition. On continued use it was also found that twice daily topical application of an amphoteric or pseudoamphoteric composition containing an alpha hydroxyacid or the related compound of the instant invention prevented the development of new dry skin lesions.

2. Severe Dry Skin

In severe dry skin, the skin lesions are different from the ordinary dry skin. A main cause of severe dry skin is inherited genetic defects of the skin. The involved skin is hyperplastic, fissured and has thick adherent scales. The degree of thickening is such that lesions are palpably and visually elevated. The thickened adherent scales cause the surface of involved skin to be markedly rough and uneven. These two attributes of thickness and texture can be quantified to allow objective measurement of degree of improvement from topically applied test materials as follows:

In order to evaluate the amphoteric and pseudoamphoteric compositions of the instant invention, a total of 6 patients having severe dry skin conditions were treated with the compositions containing an alpha hydroxyacid or the related compound.

Tested areas were of a size convenient for topical applications, i.e., circles 5 cm in diameter demarcated with a plastic ring of that size inked on a stamp pad. The medicinal lotions or creams were topically applied by the patient in an amount sufficient to cover the treatment sites. Applications were made three times daily and without occlusive dressings. Applications were discontinued at any time when resolutions of the lesion on the treatment area was clinically judged to be complete.

The test results of amphoteric and pseudoamphoteric compositions containing the following alpha hydroxyacids or the related compounds on patients with severe dry skin are summarized as follows:

4+Effectiveness; glycolic acid, lactic acid, methyllactic acid, mandelic acid, tropic acid, atrolactic acid and pyruvic acid.

3+Effectiveness; benzilic acid, gluconolactone, malic acid, tartaric acid, citric acid, saccharic acid, methyl pyruvate, ethyl pyruvate, phenyllactic acid, phenylpyruvic acid, glucuronic acid and 3-hydroxybutanoic acid.

2+Effectiveness; mucic acid, ribonolactone, 2-hydroxydodecanoic acid, quinic acid, benzoylformic acid and methyl benzoylformate.

3. Psoriasis

The involved skin in psoriasis is hyperplastic (thickened), erythematous (red or inflamed), and has thick adherent scales. The degree of thickening is such that lesions are elevated up to 1 mm above the surface of adjacent normal skin; erythema is usually an intense red; the thickened adherent scales cause the surface of involved skin to be markedly rough and uneven. These three attributes of

|  | DEGREE OF IMPROVEMENT | | | | |
| --- | --- | --- | --- | --- | --- |
|  | None (0) | Mild (1+) | Moderate (2+) | Substantial (3+) | Complete (4+) |
| Thickness | Highly elevated | Detectable reduction | Readily apparent reduction | Barely elevated | Normal thickness |
| Texture | Visibly rough | Palpably rough | Uneven but not rough | Slightly uneven | Visibly and palpably smooth |

By means of such parameters, degrees of change in lesions can be numerically recorded and comparisons made of one treated site to another.

thickness, color and texture can be quantified to allow objective measurement of degree of improvement from topically applied test materials as follows.

|  | DEGREE OF IMPROVEMENT | | | | |
| --- | --- | --- | --- | --- | --- |
|  | None (0) | Mild (1+) | Moderate (2+) | Substantial (3+) | Complete (4+) |
| THICKNESS | Highly elevated | Detectable reduction | Readily apparent reduction | Barely elevated | Normal thickness |
| TEXTURE | Visibly rough | Palpably rough | Uneven but not rough | Slightly uneven | Visibly and palpably smooth |
| COLOR | Intense Red | Red | Dark Pink | Light Pink | Normal Skin Color |

By means of such parameters, degree of improvement in psoriatic lesions can be numerically recorded and comparisons made of one treated site to another.

Patients having psoriasis participated in this study. Amphoteric and pseudoamphoteric compositions containing both an alpha hdyroxyacid or the related compound and a corticosteroid were prepared according to the Examples. Compositions containing only a corticosteroid were also prepared and included in the comparison test. Test areas were kept to minimal size convenient for topical application, i.e., circles approximately 4 cm in diameter. The medicinal compositions were topically applied by the patient in an amount (usually about 0.1 milliliter) sufficient to cover the test site. Applications were made two to three times daily and without occlusive dressings. Test periods usually lasted for two to four weeks. The test results on patients having psoriasis are summarized on the following table.

Topical Effects on Psoriasis of
Antipsoriatic Compositions

| Compositions* | Therapeutic Effectiveness |
| --- | --- |
| Hydrocortisone 2.5% alone | 1+ |
| With tactic acid | 2+ |
| With glycolic acid | 2+ |
| With ethyl pyruvate | 2+ |
| With methyl pyruvate | 2+ |
| With benzilic acid | 2+ |
| With pyruvic acid | 2+ |
| With methyllactic acid | 2+ |
| Hydrocortisone 17-valerate 0.2% alone | 2+ |
| With tactic acid | 3+ |
| With glycolic acid | 3+ |
| With benzilic acid | 3+ |
| With ethyl pyruvate | 3+ |
| With methyl pyruvate | 3+ |
| With gluconolactone | 3+ |
| With pyruvic acid | 3+ |
| Betamethasone dipropionate 0.05% alone | 3+ |
| With lactic acid | 4+ |
| With glycolic acid | 4+ |
| With ethyl pyruvate | 4+ |
| With methyl pyruvate | 4+ |
| With mandelic acid | 4+ |
| With benzilic acid | 4+ |
| Clobetasol propionate 0.05% alone | 3+ |
| With lactic acid | 4+ |
| With glycolic acid | 4+ |
| with ethyl pyruvate | 4+ |
| With methyl pyruvate | 4+ |
| With methyllactic acid | 4+ |
| With mandelic acid | 4+ |
| With tropic acid | 4+ |
| With benzilic acid | 4+ |

*Except the "alone" preparations, all others were amphoteric or pseudoamphoteric compositions containing 0.2 to 2M alpha hydroxyacids or related compounds.

We have also found that an amphoteric or pseudoamphoteric composition containing an alpha hydroxyacid or the related compound in combination with an antimetabolite agent such as 5-fluorouracil with or without additional incorporation of a corticosteroid is therapeutically effective for topical treatment of psoriasis.

4. Eczema

In a topical treatment of eczema patients, hydrocortisone alone at 2.5% or hydrocortisone 17-valerate alone at 0.2% would achieve only 2+ improvement, and betamethasone dipropionate or clobetasol propionate alone at 0.05% would achieve only a 3+ improvement en all the eczema patients tested. Test results of amphoteric and pseudoamphoteric compositions containing both a corticosteroid and one of the following alpha hydroxyacids or the related compounds are shown as follows:

3+ Effectiveness; hydrocortisone 2.5% or hydrocortisone 17-valerate 0.2% plus lactic acid, glycolic acid, mandelic acid, ethyl pyruvate, gluconolactone, benzilic acid or ribonolactone.

4+ Effectiveness; betamethasone dipropionate or clobetasol propionate 0.05% plus lactic acid, glycolic acid, mandelic acid, ethyl pyruvate, methyl pyruvate, benzilic acid, gluconolactone, citric acid, tartaric acid or methyllactic acid.

5. Oily Skin and Skin Cleanse

Human subjects having oily skin or blemished skin as well as acne patients having extremely oily skin participated in this study. Amphoteric and pseudoamphoteric compositions containing alpha hydroxyacids or the related compounds were formulated in solution or gel form.

Each participating subject received a solution or a gel preparation containing an alpha hydroxyacid or a related compound in an amphoteric or pseudoamphoteric composition. The participating subjects were instructed to apply topically the solution or gel medication on the affected areas of forehead or other part of the face. Three times daily applications were continued for 2 to 6 weeks.

The degree of improvement of oily skin as well as the rate of improvement of acne lesions were clinically evaluated. Most participants reported that oiliness of skin disappeared within one to two weeks of topical administration, and the skin so treated became smooth and soft. Many participating subjects preferred gel preparations than solution compositions. It was found that all the participants showed substantial improvements on oily skin and acne lesions by six weeks of topical administration of amphoteric or pseudoamphoteric compositions containing alpha hydroxyacids or the related compounds of the instant invention.

Those alpha hydroxyacids and the related compounds which have been found to be therapeutically effective for oily skin and as skin cleansers include: benzilic acid, glycolic acid, lactic acid, methyllactic acid, mandelic acid, pyruvic acid, ethyl pyruvate, methyl pyruvate, tropic acid, malic acid, gluconolactone, 3-hydroxybutanoic acid, glycolide and polyglycolic acid. As a skin cleanser for oily skin or acne-prone skin, the amphoteric or pseudoamphoteric composition containing an alpha hydroxyacid or the related compound may also be incorporated with other dermatologic agents. For example, an amphoteric gel composition may consist of both an alpha hydroxyacid and erythromycin or tetracycline.

6. Acne

Amphoteric and pseudoamphoteric compositions containing alpha hydroxyacids or the related compounds of the instant invention in a solution or gel form were provided to patients having comedongenic and/or papulopustular lesions of acne. Each participating patient was instructed to apply topically the composition on the involved areas of the skin such as forehead, face and chest. Three times daily administration was continued for 6 to 12 weeks.

The degree and rate of improvement on acne lesions were clinically evaluated. It was found that acne lesions consisting mainly of comedones improved substantially after 6 to 8 weeks of topical administration with the amphoteric or the pseudoamphoteric composition containing an alpha hydroxyacid or the related compound. The time for complete clearing of comedongenic acne treated with the amphoteric or pseudoamphoteric composition of the instant invention varied from 6 to 12 weeks.

As a topical treatment for papulopustular and/or pustular acne the amphoteric or pseudoamphoteric composition containing an alpha hydroxyacid or the related compound may incorporate in addition an antiacne agent. The antiacne agents include antibiotics such as erythromycin, tetracycline, clindamycin, meclocycline and minocycline, and retinoids such as retinoic acid. Such combination compositions have been found to be therapeutically more effective for topical treatment of severe ache.

7. Age Spots

Many small and large discolored lesions, commonly called age spots on the face and the back of the hands are benign keratoses, if they are not variants of actinic keratoses. Very few of such age spots are true lentigines, therefore alpha hydroxyacids and the related compounds may be effective in eradicating most age spots without concurrent use of skin bleaching agents such as hydroquinone and monobenzone. However, additional beneficial effects have been found when a skin bleaching agent such as hydroquinone or monobenzone is also incorporated into the compositions of the instant invention for age spots involving pigmented lesions.

Amphoteric and pseudoamphoteric compositions containing alpha hydroxyacids or the related compounds, with or without incorporation of hydroquinone were provided to volunteer subjects and patients having age spot keratoses, melasma, lentigines and/or other pigmented lesions. Each participating subject received two products, i.e., with or without the addition of 2% hydroquinone to the amphoteric or pseudoamphoteric composition containing an alpha hydroxyacid or the related compound.

The volunteer subjects and patients were instructed to apply topically one medication on one side of the body such as left side of the face or on the back of the left hand, and the other medication on the other side of the body such as on right side of the face or on the back of the right hand. Specific instructions were given to the participating subjects that the medications were applied three times daily to the lesions of age spot keratoses, melasmas, lentigines and/or other pigmented lesions. Clinical photos were taken of participating subjects before the initiation of the topical treatment and every 4 weeks during the course of treatment.

At the end of 4 to 8 weeks, improvement of age spot keratoses was clinically discernible. After 4 to 6 months of topical treatment, substantial improvement of age spot keratoses occurred in the majority of subjects tested. Complete eradication of age spot keratoses occurred after 6 to 9 months of topical administration with the amphoteric or pseudoamphoteric compositions of the instant inventions.

Amphoteric or pseudoamphoteric compositions containing both an alpha hydroxyacid or the related compound and hydroquinone were judged to be more effective in eradicating pigmented age spots, melasma, lentigines and other pigmented lesions.

The alpha hydroxyacids and the related compounds which have been found to be therapeutically effective for age spots with or without combination with hydroquinone include glycolic acid, lactic acid, methyllactic acid, mandelic acid, pyruvic acid, methyl pyruvate, ethyl pyruvate, benzilic acid, gluconolactone, malic acid, tartaric acid, citric acid and tropic acid. For flat or slightly elevated seborrheic keratoses on the face and/or the back of the body, amphoteric or pseudoamphoteric compositions containing higher concentrations of alpha hydroxyacids or the related compounds have been found to be effective in eradicating such lesions.

Actinic keratoses may be successfully treated with amphoteric or pseudoamphoteric compositions containing alpha hydroxyacids or the related compounds in combination with an antimetabolite agent such as 5-fluorouracil.

8. Warts

Eradications of common warts by topical application of amphoteric or pseudoamphoteric compositions require higher than usual concentrations of alpha hydroxyacids or the related compounds in the formulations. The amphoteric or pseudoamphoteric compositions were formulated as a liquid or light gel form, and dispensed usually as 0.5–1 ml aliquots in small vials.

Topical applications were made discreetly to wart lesions by adult patients or by responsible adult family members. For ordinary usual warts of hands, fingers, palms and soles topical applications were made 2 to 4 times daily, and were continued for 2 to 6 weeks. Generally, the overlying stratum corneum of the wart lesion change in appearance after several weeks topical application of the composition. In most cases, the wart lesion simply fell off. The skin then healed normally without forming any scars.

We have also found that when a dermatologic agent such as 5-fluorouracil is incorporated into the amphoteric or pseudoamphoteric compositions containing alpha hydroxyacids or the related compounds, the medications have been very effective for topical treatment of warts without using higher concentrations of alpha hydroxyacids or the related compounds.

The alpha hydroxyacids and the related compounds which have been found to be therapeutically effective for topical treatment of warts with or without incorporation of 5-fluorouracil include glycolic acid, lactic acid, pyruvic acid, ethyl pyruvate, methyl pyruvate and mandelic acid.

Topical formulations and compositions containing specific alpha hydroxyacids, alpha ketoacids or the related compounds at full strengths or high to intermediate concentrations prepared according to Examples 54 and 55, without utilizing amphoteric or pseudoamphoteric systems, have also been tested for ordinary warts of the hands, fingers, palms and soles. Participating patients have been advised to apply a small drop of the medication with a toothpick or a fine caliber brush to the center of a wart lesion only. Prescirbed applications have been 3 to 6 times daily, and are continued until the patient feels pain.

For the more rough-surfaced wart, the duration of application has been as short as one or a few days. For lesions with more compact, less permeable stratum corneum, the time to experience gpain has been longer. Frequency and duration of applications have been modified according to other clinical responses and reactions of lesions, and the patient or responsible family member is instructed accordingly.

For example, some clinical manifestations other than pain have also been used as a signal to interrupt application. These manifestations have included distinct blanching of the lesions or distinct peripheral erythema. Very often, discomfort is the usual signal of clinical reactions.

Generally, the overlying stratum corneum of the wart lesions became loose, and the whole wart lesion simply fell off. The skin then healed normally without forming any scars.

9. Athlete's Foot and Nail Infections

Amphoteric and pseudoamphoteric compositions containing both an antifungal agent and one of the alpha hydroxyacids or the related compounds were provided to patients having frequent recurrence of fungal infections involving the foot. The antifungal agents include clotrimazole, miconazole, ketoconazole and griseofulvin. When both feet but not toe nails were involved in the infection, the patients were instructed to apply topically the compositions of the instant invention on the left foot, and a brand-name antifungal product on the right foot. Three times daily applications were continued for one to four weeks. The degree and rate of improvement on skin lesions were clinically evaluated, and comparison was made one side of the body against the other. It was found that the skin lesions improved much faster with the amphoteric or pseudoamphoteric compositions containing both the antifungal agent and the alpha hydroxyacid or the related compound. The alpha hydroxyacids or the related compounds seemed to enhance the efficacies of the antifungal agents, and also to eliminate the discomforts such as itching, tingling, burning and irritation due to fungal infections. When toe nails were not involved the infected skin generally healed within one to two weeks from topical application of the amphoteric or pseudoamphoteric composition containing both an antifungal agent and an alpha hydroxyacid or the related compound.

Fungal infections of the nails are very difficult to treat, because antifungal products to date are not therapeutically effective for topical treatment of nails. One of the reasons is that most antifungal drugs have not been formulated as bioavailable forms in the commercial products. When tow nails were involved in the infections, patients were provided with amphoteric or pseudoamphoteric compositions containing in combination an antifungal agent and an alpha hydroxyacid or an alpha ketoacid at higher concentrations ranging from 20 to 99%, dispensed as 1–2 ml aliquots in small vials. The patients were instructed to apply topically the compositions discreetly to the infected nail surface by means of a fine calibre paint brush the technique was the same as for application of nail polish, that is careful avoidance of contact with lateral nail folds or any peri-ungual skin. Once or twice daily applications were continued for 2 to 8 weeks.

As mentioned above, while brand-name antifungal products are usually not effective against fungus infections within or underneath the nail, it was found that the amphoteric or pseudoamphoteric compositions containing an antifungal agent and an alpha hydroxyacid or alpha ketoacid were therapeutically effective in eradicating fungal infections of the nails. Such treatment may cause in some instances the treated nail plate to become loose and eventually fell off from the nail bed. This happened quite naturally without any feeling of pain nor bleeding, and the skin lesion healed quickly with normal growth of a new nail.

10. Wrinkles

Wrinkles of skin may be due to natural aging and/or sun damage. Most fine wrinkles on the face are due to natural or innate aging, while coarse wrinkles on the face are the consequence of actinic or sun damage. Although the real mechanism of wrinkles formation in the skin is still unknown, it has been shown that visible fine wrinkles are due to diminution in the number and diameter of elastic fibers in the papillary dermis, and also due to atrophy of dermis as well as reduction in subcutaneous adipose tissue. Histopathology and electron microscopy studies indicate that coarse wrinkles are due to excessive deposition of abnormal elastic materials in the upper dermis and thickening of the skin. At present there are no commercial products which have been found to be therapeutically effective for topical eradication of wrinkles, although retinoic acid (tretinoin) has been shown to be beneficial for sun damaged skin.

In order to determine whether the amphoteric or pseudoamphoteric composition containing the alpha hydroxyacids, alpha ketoacids or the related compounds are therapeutically effective for wrinkles, patients and volunteer subjects participated in this study. The participants were instructed to apply the formulations of the instant invention twice daily on areas of facial wrinkles for 4 to 12 months. All participants were told to avoid sun exposure, and to use sunscreen products if exposure to sunlight was unavoidable. Photographs of each side of the face for each participant were taken at the beginning of the study and repeated at one to three-month intervals. The participants were asked not to wear any facial make-up at the time of each office visit. Standardized photographic conditions were used including the use of same lot of photographic film, the same light source at two feet from the face, aimed at a locus on the frontal aspect of each cheek. Each time photographs were taken with camera aimed perpendicular to the cheek. At the end of study twenty two participants had been entered into the study for at least four months. Clinical evaluations and review of photographs have revealed substantial reductions in facial wrinkles of the temporal region and cheek area on at least one side of the face in eighteen cases. Degree of improvement and reduction in wrinkles has been evaluated and determined to be mild to moderate in six participants but very substantial in twelve participants.

The alpha hydroxyacids, alpha ketoacids and other related compounds including their lactone forms which may be incorporated into the amphoteric and pseudoamphoteric compositions for cosmetic conditions and dermatologic disorders such as dry skin, acne, age spots, keratoses, warts and skin wrinkles or in combination with other dermatologic agents to enhance therapeutic effects include the following:

(1) Alkyl Alpha Hydroxyacids

2-Hydroxyethanoic acid (Glycolic acid), 2-Hydroxypropanoic acid (Lactic acid), 2-Methyl 2-hydroxypropanoic acid (Methyllactic acid), 2-Hydroxybutanoic acid, 2-Hydroxypentanoic acid, 2-Hydroxyhexanoic acid, 2-Hydroxyheptanoic acid, 2-Hydroxyoctanoic acid, 2-Hydroxynonanoic acid, 2-Hydroxydecanoic acid, 2-Hydroxyundecanoic acid, 2-Hydroxydodecanoic acid (Alpha hydroxylauric acid), 2-Hydroxytetradecanoic acid (Alpha hydroxymyristic acid), 2-Hydroxyhexadecanoic acid (Alpha hydroxypalmitic acid), 2-Hydroxyoctadecanoic acid (Alpha hydroxystearic acid), 2-Hydroxyeicosanoic acid (Alpha hydroxyarachidonic acid).

(2) Aralkyl and Aryl Alpha Hydroxyacids

2-Phenyl 2-hydroxyethanoic acid (Mandelic acid), 2,2-Diphenyl 2-hydroxyethanoic acid (Benzilic acid), 3-Phenyl 2-hydroxypropanoic acid (Phenyllactic acid), 2-Phenyl 2-methyl 2-hydroxyethanoic acid (Atrolactic acid), 2-(4'-Hydroxyphenyl) 2-hydroxyethanoic acid, 2-(4'-Chlorophenyl) 2-hydroxyethanoic acid, 2-(3'-Hydroxy-4'-methoxyphenyl) 2-hydroxyethanoic acid, 2-(4'-Hydroxy-3'-methoxyphenyl) 2-hydroxyethanoic acid, 3-(2'-Hydroxyphenyl) 2-hydroxypropanoic acid, 3-(4'-Hydroxyphenyl) 2-hydroxypropanoic acid, 2-(3',4'-Dihydroxyphenyl) 2-hydroxyethanoic acid.

(3) Polyhydroxy Alpha Hydroxyacids 2,3-Dihydroxypropanoic acid (Glyceric acid), 2,3,4-Trihydroxybutanoic acid (Isomers; erythronic acid, threonic acid), 2,3,4,5-Tetrahydroxypentanoic acid (Isomers; ribonic acid, arabinoic acid, xylonic acid, lyxonic acid), 2,3,4,5,6-Pentahydroxyhexanoic acid (Isomers; aldonic acid, altronic acid, gluconic acid, mannoic acid, gulonic acid, idonic acid, galactonic acid, talonic acid),. 2,3,4,5,6,7-Hexahydroxyheptanoic acid (Isomers; glucoheptonic acid, galactoheptonic acid, etc.)

(4) Polycarboxylic Alpha Hydroxyacids

2-Hydroxypropane-1,3-dioic acid (Tartronic acid), 2-Hydroxybutane-1,4-dioic acid (Malic acid), 2,3-Dihydroxybutane-1,4-dioic acid (Tartaric acid), 2-Hydroxy-2-carboxypentane-1,5-dioic acid (Citric acid), 2,3,4,5-Tetrahydroxyhexane-1,6-dioic acid (Isomers; saccharic acid, mucic acid, etc.)

(5) Alpha Hydroxyacid Related Compounds

Ascorbic acid, quinic acid, isocitric acid, tropic acid, 3-chlorolactic acid, trethocanic acid, cerebronic acid, citramalic acid, agaricic acid, 2-hydroxynervonic acid and aleuritic acid.

(6) Alpha Ketoacids and Related Compounds

2-Ketoethanoic acid (Glyoxylic acid), Methyl 2-ketoethanoate, 2-Ketopropanoic acid (Pyruvic acid), Methyl 2-ketopropanoate (Methyl pyruvate), Ethyl 2-ketopropanoate (Ethyl pyruvate), Propyl 2-ketopropanoate (Propyl pyruvate), 2-Phenyl-2-ketoethanoic acid (Benzoylformic acid), Methyl 2-phenyl-2-ketoethanoate (Methyl benzoylformate), Ethyl 2-phenyl-2-ketoethanoate (Ethyl benzoylformate), 3-Phenyl-2-ketopropanoic acid (Phenylpyruvic acid), Methyl 3-phenyl-2-ketopropanoate (Ethyl phenylpyruvate), 2-Ketobutanoic acid, 2-Ketopentanoic acid, 2-Ketohexanoic acid, 2-Ketoheptanoic acid, 2-Ketooctanoic acid, 2-Ketododecanoic acid, Methyl 2-ketooctanoate The amphoteric and pseudoamphoteric compounds which may be incorporated into the compositions of the instant invention for cosmetic and dermatologic conditions include amino acids, peptides, polypeptides, proteins and the like compounds such as creatinine and creatine.

The dimeric and polymeric forms of alpha hydroxyacids and the related compounds which may be incorporated into the compositions of the instant invention include acyclic esters and cyclic ester; for example, glycolyl glycollate, lactyl lactate, glycolide, lactide, polyglycolic acid and polylactic acid.

The invention may be embodied in other specific forms without departing from the spirit or essential characteristics thereof. The present embodiments are therefore to be considered in all respects as illustrative and not restrictive, the scope of the invention being indicated by the appended claims and all changes which come within the meaning and equivalency of the claims are therefore intended to be embraced therein.

What is claimed is:

1. Method of visibly reducing a human skin wrinkle comprising topically applying to said wrinkle a composition comprising isocitric acid or a topically effective salt thereof, in an amount and for a period of time sufficient to visibly reduce said wrinkle.

2. The method according to claim 1, wherein said isocitric acid is in the form of a free acid.

3. The method according to claim 1, wherein said isocitric acid is in the form of a salt.

4. The method according to claim 1, wherein said isocitric acid or topically effective salt thereof is applied periodically for a period of time sufficient to achieve at least a visibly mild to moderate reduction of said wrinkle.

5. The method according to claim 1, wherein said isocitric acid or topically effective salt thereof is applied periodically for a period of time sufficient to achieve at least a substantial reduction of said wrinkle.

6. The method according to claim 1, wherein said period of time is at least two months.

7. The method according to claim 1, wherein said period of time is at least three months.

8. The method according to claim 1, wherein said period of time is at least four months.

9. The method according to claim 1, wherein said topical application is on a daily basis.

10. The method according to claim 1, wherein said wrinkle is a fine wrinkle.

11. The method according to claim 1, wherein said wrinkle is a coarse wrinkle.

12. The method according to claim 1, wherein said wrinkle is the result of actinic or sun damage.

13. The method according to claim 1, wherein said isocitric acid or topically effective salt thereof is the principal ingredient responsible for said reduction.

14. A method for reversing or retarding the effect of aging on human facial skin, said effect being a change in the dermis that results from natural or innate aging or exposure to actinic radiation, said change in the dermis selected from the group consisting of a diminution in the number and diameter of elastic fibers in the papillary dermis, atrophy of the dermis, reduction in subcutaneous adipose tissue and deposition of abnormal elastic materials in the upper dermis, said method comprising topically applying to said facial skin a composition comprising isocitric acid or a topically effective salt thereof, in an amount and for a period of time sufficient to reverse or prevent said change in the dermis, wherein said isocitric acid or a topically effective salt thereof is the principal ingredient responsible for said reversing or retarding.

15. The method according to claim 14, wherein said isocitric acid is in the form of a free acid or a salt.

16. The method according to claim 14, wherein said period of time is at least three months.

17. The method according to claim 14, wherein said period of time is at least four months.

18. The method according to claim 14, wherein said topical application is on a daily basis.

19. The method according to claim 14, wherein said change in the dermis results from natural or innate aging.

20. The method according to claim 14, wherein said change in the dermis results from exposure to actinic radiation.

* * * * *